United States Patent
Kawamura et al.

(10) Patent No.: US 9,198,598 B2
(45) Date of Patent: Dec. 1, 2015

(54) MAGNETIC RESONANCE IMAGING APPARATUS AND SAR ADJUSTMENT METHOD

(75) Inventors: Miyuki Kawamura, Tokyo (JP); Kosuke Ito, Tokyo (JP); Hisako Nagao, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 453 days.

(21) Appl. No.: 13/638,475

(22) PCT Filed: Mar. 24, 2011

(86) PCT No.: PCT/JP2011/057135
§ 371 (c)(1),
(2), (4) Date: Sep. 28, 2012

(87) PCT Pub. No.: WO2011/122430
PCT Pub. Date: Oct. 6, 2011

(65) Prior Publication Data
US 2013/0023753 A1   Jan. 24, 2013

(30) Foreign Application Priority Data

Mar. 31, 2010 (JP) ................................. 2010-080145

(51) Int. Cl.
| A61B 5/055 | (2006.01) |
| G01R 33/28 | (2006.01) |
| G01R 33/36 | (2006.01) |
| G01R 33/54 | (2006.01) |

(52) U.S. Cl.
CPC .............. *A61B 5/055* (2013.01); *G01R 33/288* (2013.01); *G01R 33/36* (2013.01); *G01R 33/543* (2013.01); *G01R 33/546* (2013.01)

(58) Field of Classification Search
CPC combination set(s) only.
See application file for complete search history.

(56) References Cited

U.S. PATENT DOCUMENTS

| 6,687,527 B1 | 2/2004 | Wu et al. |
| 2003/0095150 A1 | 5/2003 | Trevino et al. |
| 2004/0017195 A1 | 1/2004 | Kassai et al. |
| 2007/0096735 A1 | 5/2007 | Morich et al. |
| 2011/0148412 A1 | 6/2011 | Kanazawa |

FOREIGN PATENT DOCUMENTS

| JP | 2003-319919 | 11/2003 |
| JP | 2005-501624 | 1/2005 |

(Continued)

OTHER PUBLICATIONS

International Search Report in connection with PCT/JP2011/057135.
(Continued)

*Primary Examiner* — Katherine Fernandez
*Assistant Examiner* — Farshad Negarestan
(74) *Attorney, Agent, or Firm* — Cooper & Dunham LLP

(57) ABSTRACT

Desired imaging is performed within the SAR restriction without changing the imaging conditions set in advance when SAR exceeds an upper limit. In order to do so, in imaging of an object performed by combination of a plurality of pulse sequences, a SAR graph showing a temporal change in the predicted SAR value of each pulse sequence is displayed. When the predicted SAR value of the pulse sequence is the same as or exceeds the upper SAR limit, the exchange of such pulse sequences or the insertion of a waiting time is performed.

20 Claims, 25 Drawing Sheets

(56) References Cited

FOREIGN PATENT DOCUMENTS

| | | |
|---|---|---|
| JP | 2011-143235 | 7/2011 |
| WO | WO2010/001747 | 1/2010 |

OTHER PUBLICATIONS

C. Lin et al. (2006), "Integration of Scan Time Reduction Techniques with Rearranged Elliptical Centric k-Space Acquisition for 3DTOF MRA at 3.0T", Proc Intl Soc Mag Reson Med 14, p. 809.

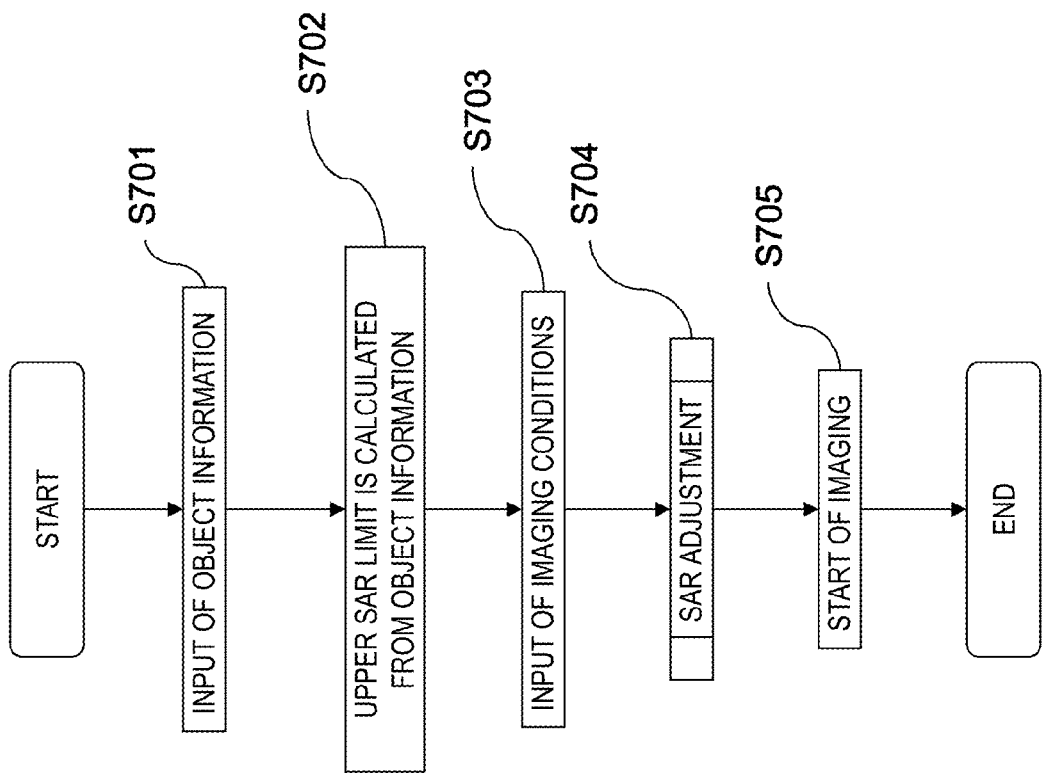

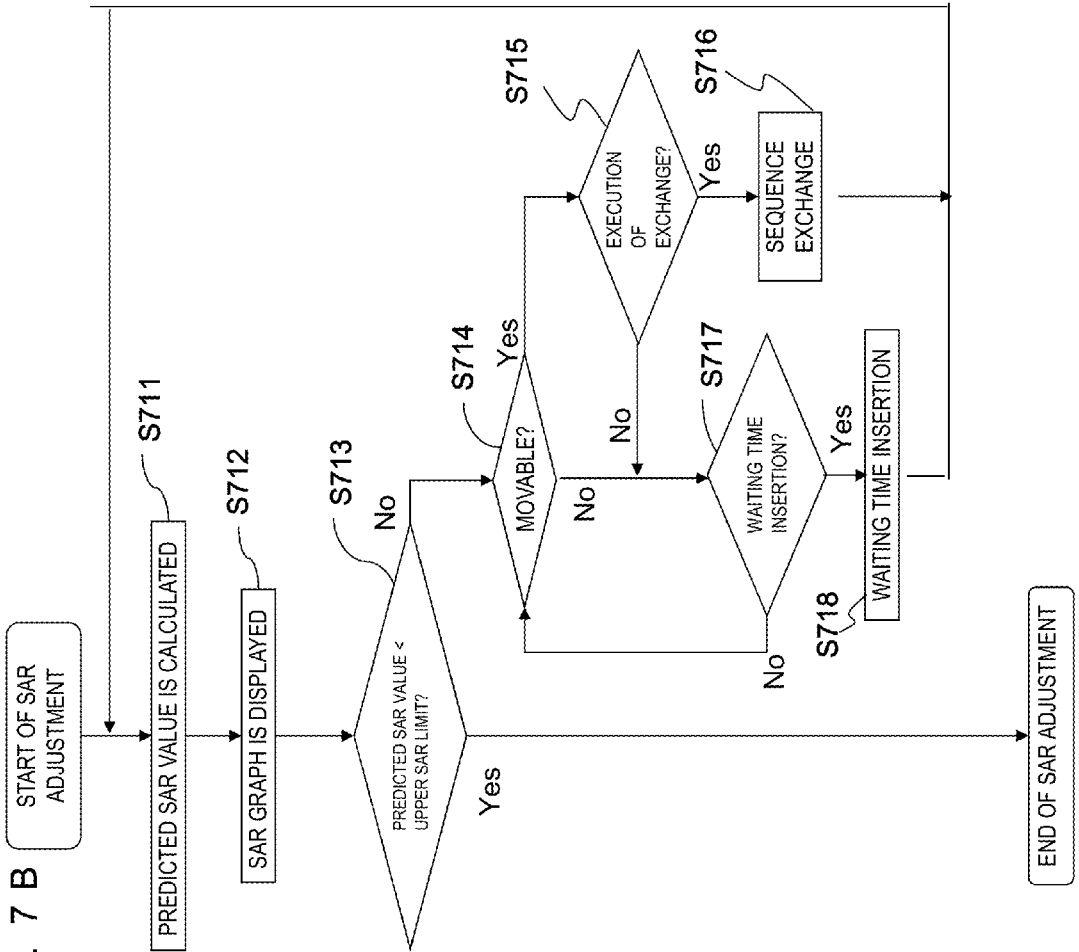

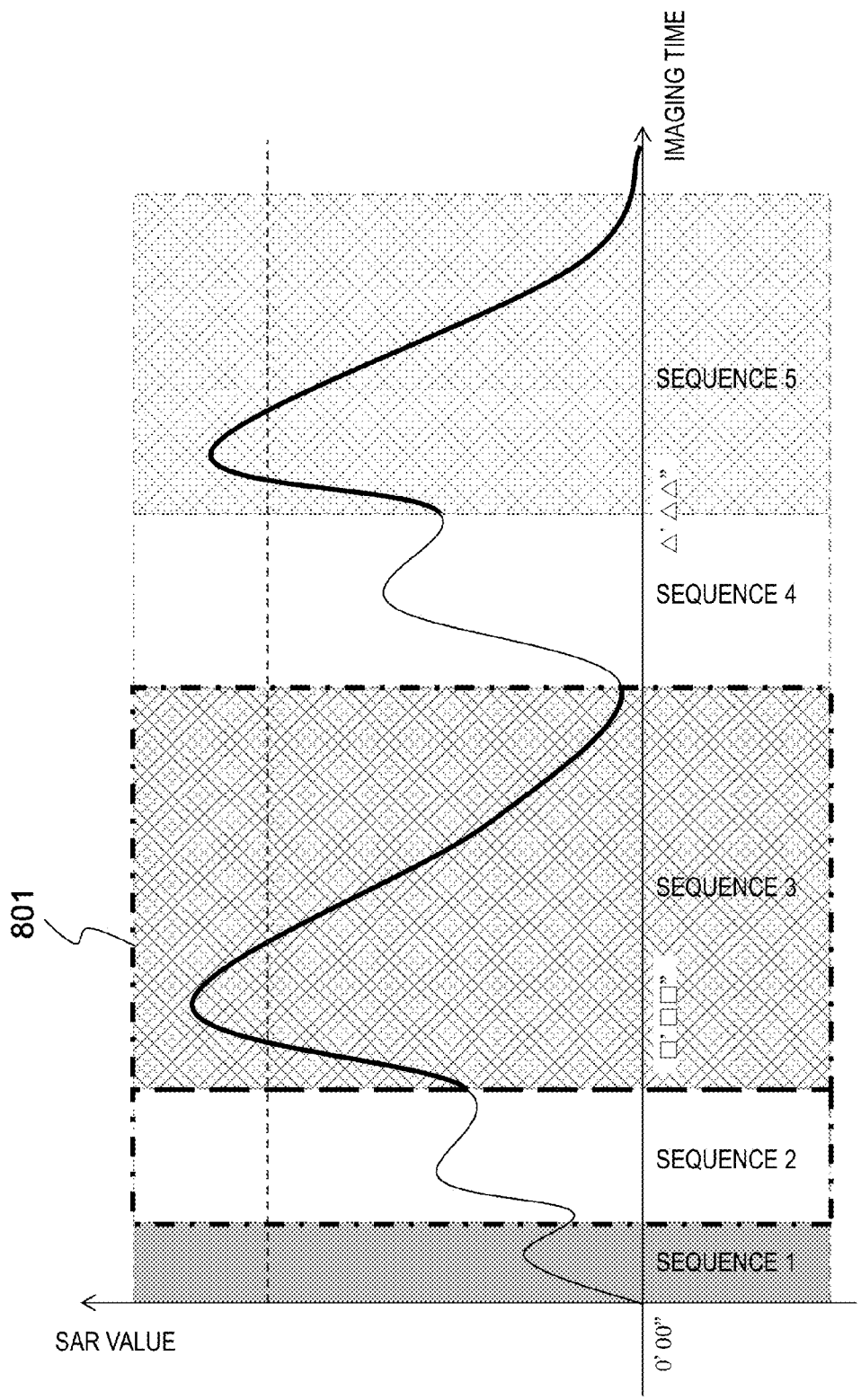

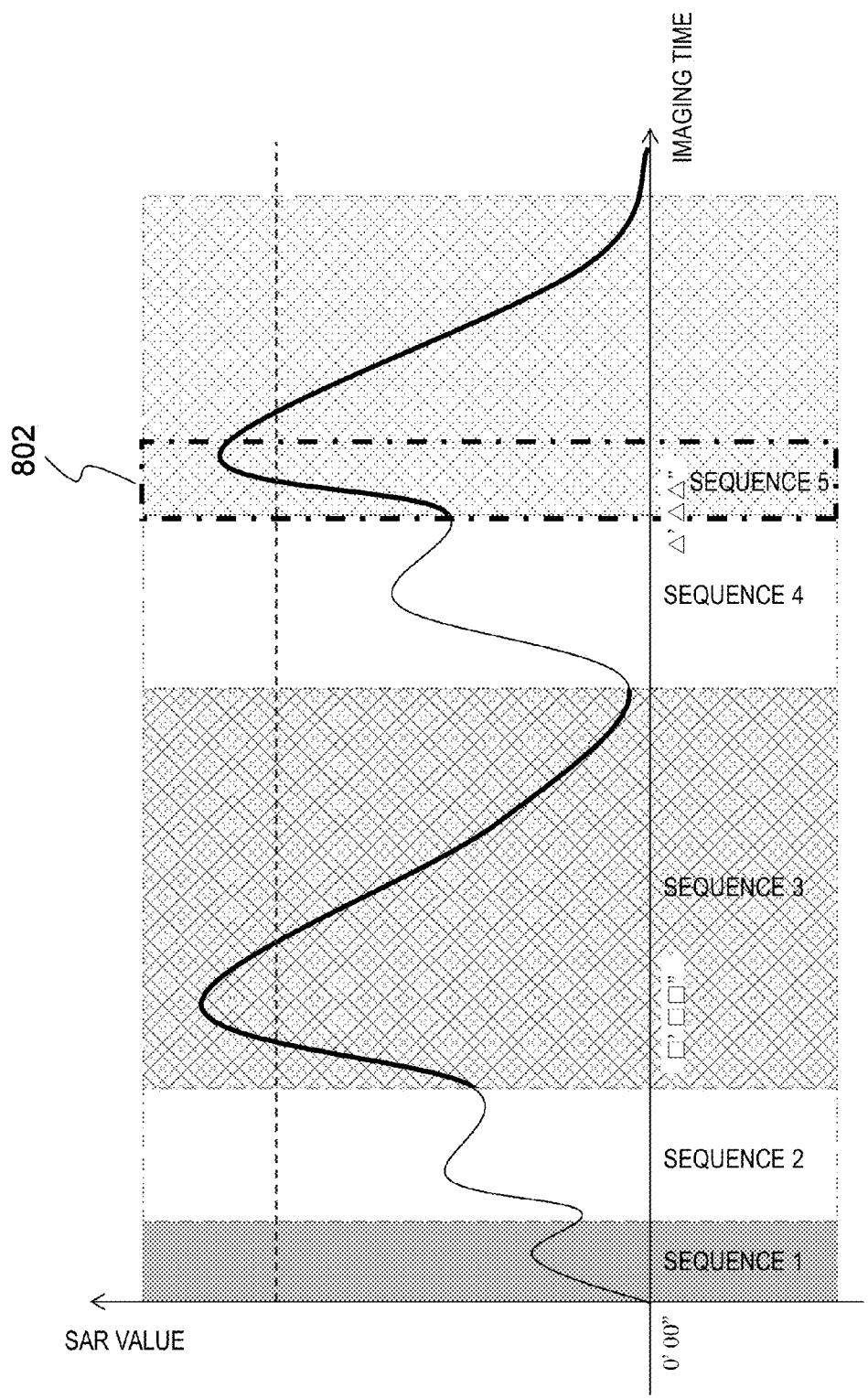

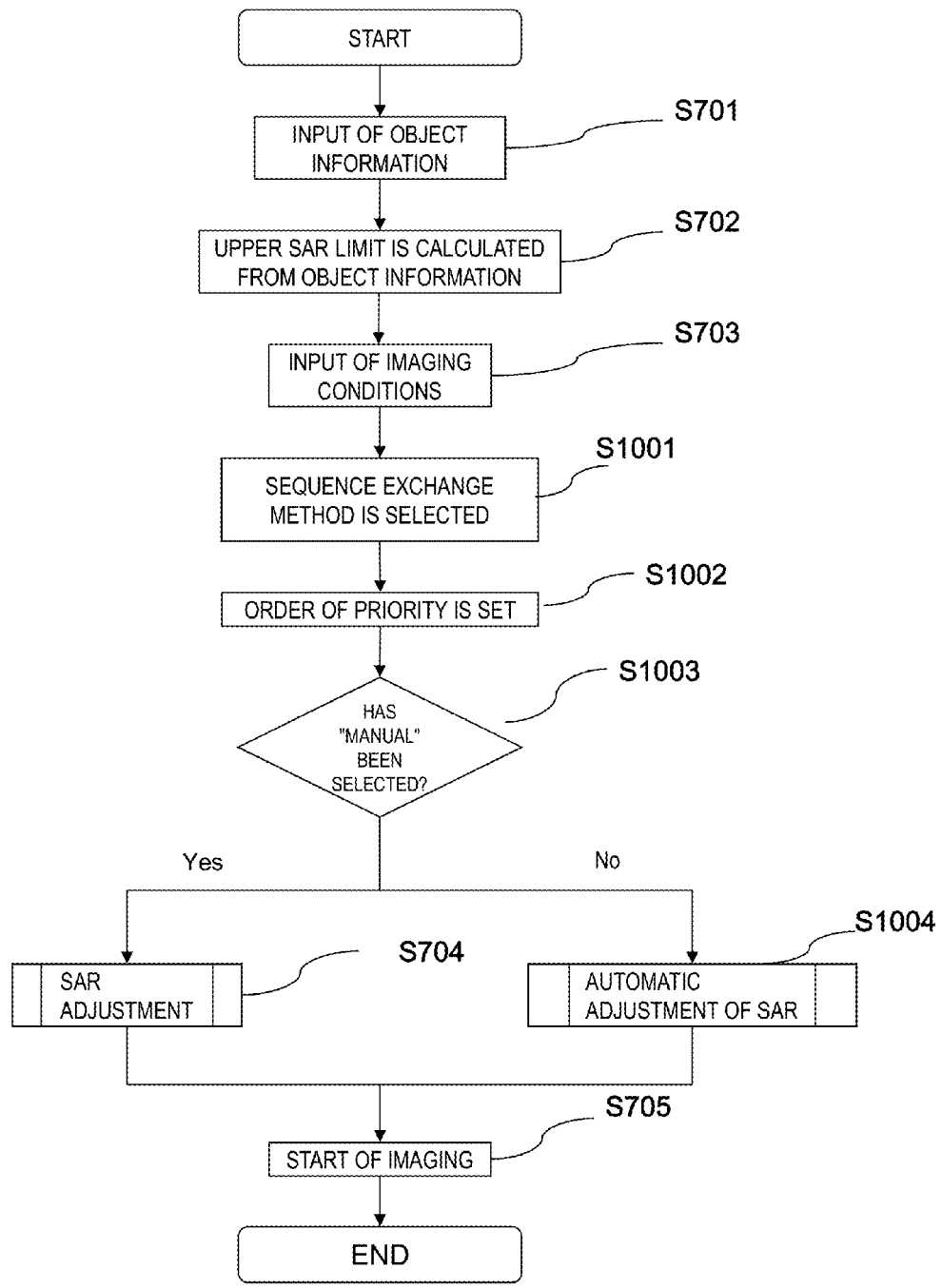
F I G. 10A

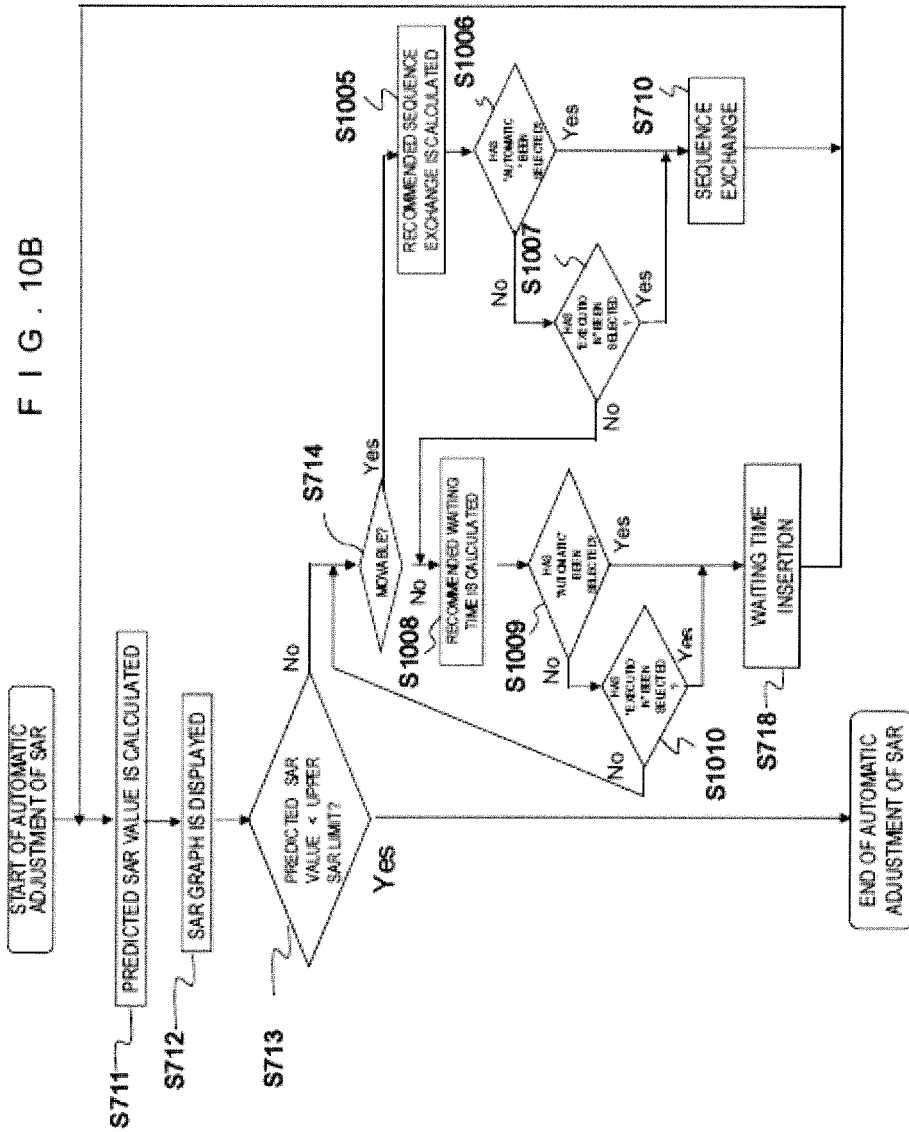

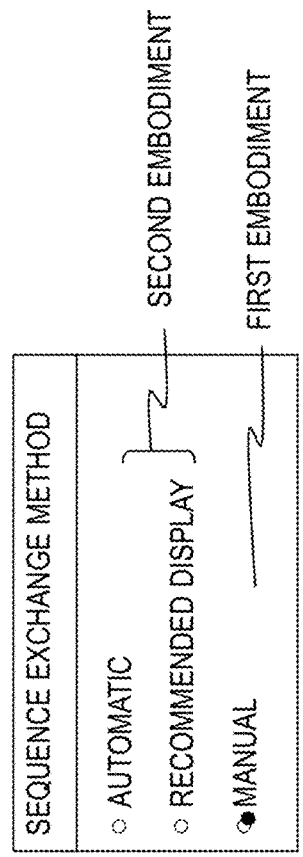

F I G . 12

(a)

SAR VALUE EXCEEDS UPPER LIMIT.
DO YOU WANT TO EXCHANGE SEQUENCES 2
AND 3 WITH EACH OTHER?

Yes   No (b)

SAR VALUE EXCEEDS UPPER LIMIT.
DO YOU WANT TO INSERT WAITING TIME?

Yes   No

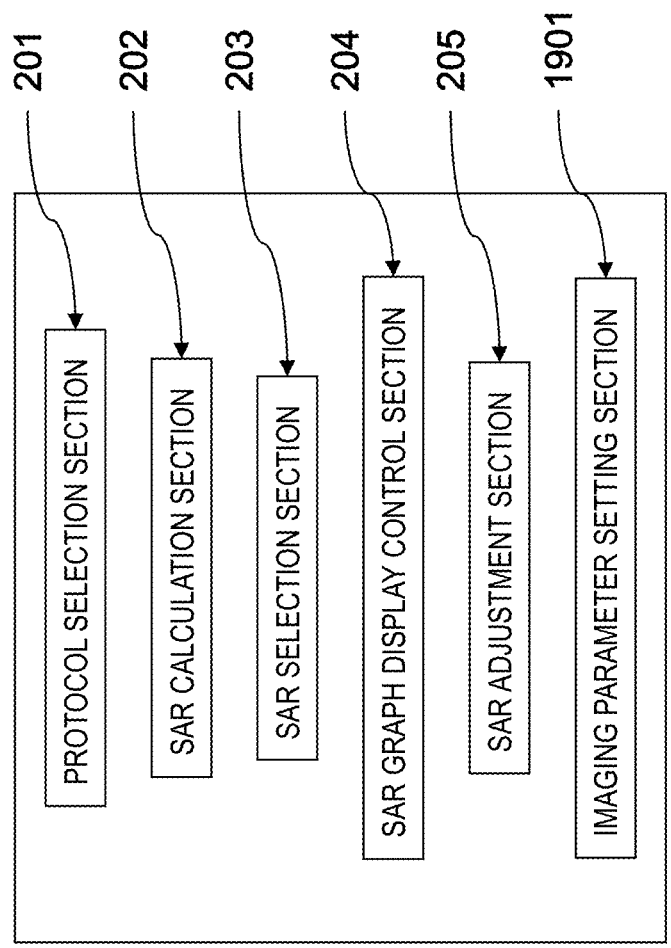
F I G . 19

MAGNETIC RESONANCE IMAGING APPARATUS AND SAR ADJUSTMENT METHOD

TECHNICAL FIELD

The present invention relates to a technique for adjusting SAR, which is one of the indices indicating electromagnetic wave energy absorbed by an object at the time of imaging, in a magnetic resonance imaging (hereinafter, referred to as "MRI") apparatus.

BACKGROUND ART

The MRI apparatus is an apparatus which measures a nuclear magnetic resonance (hereinafter, referred to as NMR) signal generated by an object, especially, the spin of nuclei which form human tissue and images the morphology or functions of the head, abdomen, limbs, and the like in a two-dimensional manner or in a three-dimensional manner. In the imaging, different phase encoding is given to NMR signals by the gradient magnetic field and frequency encoding is also given to the NMR signals, and the NMR signals are measured as time-series data. The measured NMR signals are reconstructed as an image by a two-dimensional or three-dimensional Fourier transform.

In the above-described MRI apparatus, in order to induce a nuclear magnetic resonance phenomenon, a high-frequency magnetic field pulse (hereinafter, referred to as an "RF pulse") which is an electromagnetic wave is emitted to an object. Therefore, as one of the clinical safety standards at the time of using an MRI apparatus, there is electromagnetic wave energy absorbed by an object. According to IEC60601-2 -33, $2^{nd}$ edition, the amount of absorption of electromagnetic wave energy per unit time and unit mass is set as SAR (Specific Absorption Rate) and is defined by the following Expressions, and SAR is restricted so that the object is not irradiated with an electromagnetic wave equal to or greater than the upper limit.

$$\text{Whole body } SAR \ [W/\text{kg}] = \frac{W[W]}{M[\text{kg}]} \quad (1)$$

$$\text{Body part } SAR \ [W/\text{kg}] = \frac{W_p[W]}{M_p[\text{kg}]} \quad (2)$$

Local $SAR$ [W/kg] = (3)
Energy per unit time absorbed by an arbitrary 10 g

Here, the whole body SAR is calculated by dividing electromagnetic wave energy absorbed by the whole body of the object by the mass of the object, the body part SAR is calculated by dividing electromagnetic wave energy absorbed by a target portion of the object by the mass of the target portion of the object, and the local SAR is electromagnetic wave energy per unit time absorbed by an arbitrary 10 g.

PTL 1 discloses a method of comparing the body part SAR calculated from the physical size information of the object with its upper limit and prompting the operator to change the imaging conditions when the body part SAR exceeds the upper limit.

In addition, PTL 2 discloses a method of calculating an optimal upper limit of the body part SAR not from an imaging part but from a body part to which an RF pulse is actually emitted.

CITATION LIST

Patent Literature
[PTL 1] JP-A-2006-95278
[PTL 2] JP-A-2009-72571
[PTL 3] WO2010001747

SUMMARY OF INVENTION

Technical Problem

In PTL 1 and PTL 2, however, a method of reducing SAR without changing the imaging conditions when SAR exceeds the upper limit is not taken into consideration. If the imaging conditions are changed, it may be difficult to acquire an image with desired quality (contrast or the like).

Therefore, it is an object of the invention to provide a technique for performing desired imaging within the SAR restriction without changing the imaging conditions set in advance when SAR exceeds an upper limit at the time of imaging using an MRI apparatus.

Solution to Problem

In order to achieve the above-described object, in the invention, in imaging of an object performed by combination of a plurality of pulse sequences, a SAR graph showing a temporal change in the predicted SAR value of each pulse sequence is displayed. When the predicted SAR value of the pulse sequence is the same as or exceeds the upper SAR limit, the exchange of such pulse sequences or the insertion of a waiting time is performed.

Specifically, an MRI apparatus of the invention includes: an RF pulse control unit that controls emission of an RF pulse to an object in imaging of the object performed by combination of a plurality of pulse sequences; a SAR calculation unit that calculates a predicted SAR value which is a predicted value of electromagnetic wave energy absorbed by the object by the emission of the RF pulse; a SAR adjustment unit that adjusts execution of the plurality of pulse sequences such that the predicted SAR value becomes less than the upper limit; and a display unit that displays the predicted SAR value, and is characterized in that the SAR calculation unit calculates a temporal change in the predicted SAR value of each of the pulse sequences and a SAR graph display control unit that creates a SAR graph showing the temporal change in the predicted SAR value of each of the pulse sequences and displays the SAR graph on the display unit is provided.

In addition, a SAR adjustment method of the invention includes: a step of calculating a temporal change in a predicted SAR value of each pulse sequence in imaging of an object performed by combination of a plurality of pulse sequences; a step of displaying a SAR graph showing a temporal change in a predicted SAR value of each pulse sequence; a step of exchanging movable pulse sequences among the plurality of pulse sequences or inserting a waiting time between some of the plurality of pulse sequences; a step of recalculating a temporal change in the predicted SAR value of each pulse sequence after the pulse sequence exchange or the waiting time insertion; and a step of updating the SAR graph so that the pulse sequence exchange or the waiting time insertion and the recalculated predicted SAR value are displayed.

Advantageous Effects of Invention

According to the MRI apparatus and the SAR adjustment method of the invention, when SAR exceeds an upper limit, it is possible to perform desired imaging within the SAR restriction without changing the imaging conditions set in advance.

BRIEF DESCRIPTION OF DRAWINGS

FIG. 7A is an entire flow chart showing the process flow of the first embodiment.

FIG. 7B is a flow chart showing the process flow of the first embodiment, and is a view showing the detailed process flow of step S704.

FIG. 8A is a view showing the display mode of a SAR graph, and is a view showing an example of the display mode of exchangeable pulse sequences.

FIG. 8B is a view showing the display mode of a SAR graph, and is a view showing an example of the display mode of a waiting time region recommended to be inserted.

FIG. 10A is an entire flow chart showing the process flow of a second embodiment.

FIG. 10B is a flow chart showing the process flow of the second embodiment, and is a view showing the detailed process flow of step S1004.

FIG. 11 is a view showing an example of menu display for selecting a pulse sequence exchange method from "Automatic", "Recommended display", and "Manual".

FIG. 12 is a message display for confirmation of an operator, where (a) is an example of message display in order for the operator to confirm whether or not the recommended exchange of pulse sequences can be executed and (b) is a view showing an example of message display in order for the operator to confirm whether or not the recommended waiting time insertion can be executed.

FIG. 19 is a functional block diagram showing each function of an arithmetic processing unit related to the third embodiment.

DESCRIPTION OF EMBODIMENTS

Figure 1:
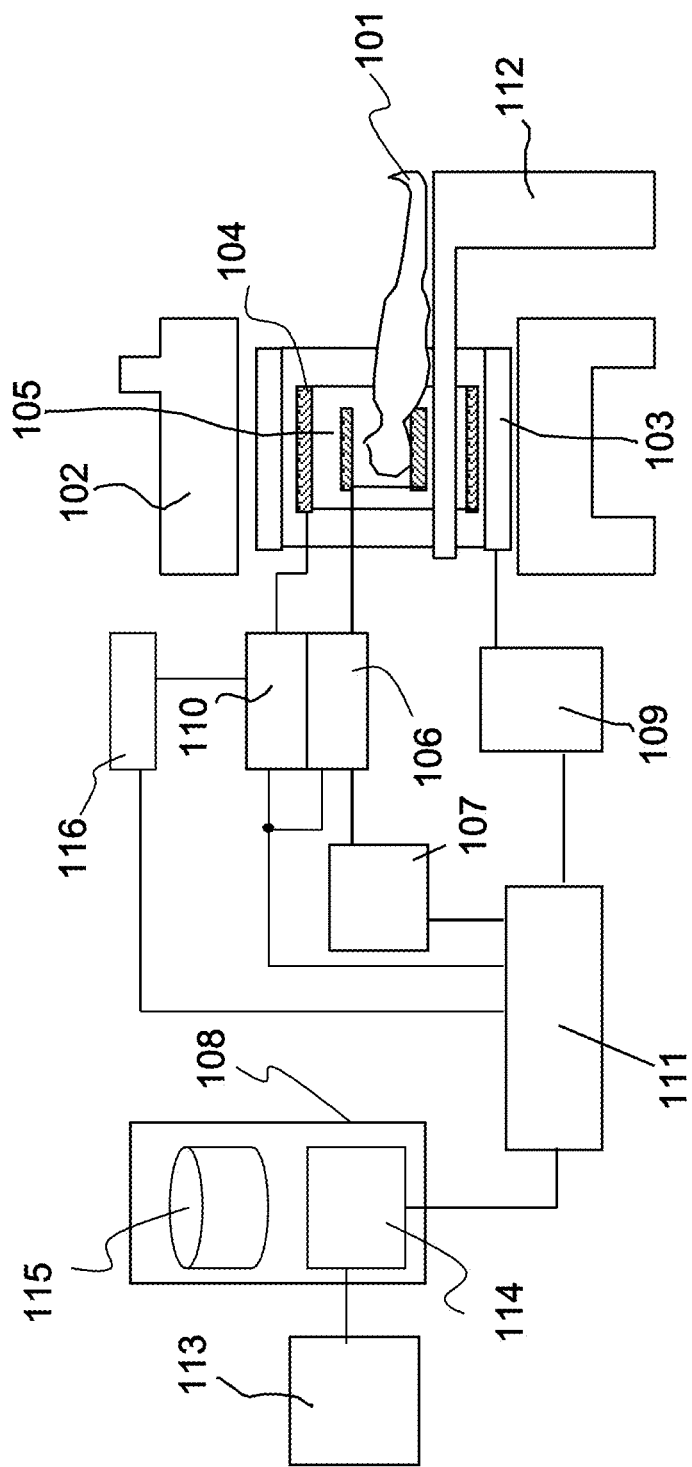
FIG. 1 is a block diagram showing the overall configuration of an embodiment of an MRI apparatus related to the invention.

Hereinafter, preferred embodiments of an MRI apparatus of the invention will be described in detail according to the accompanying drawings. In addition, in all drawings for explaining the embodiments of the invention, the same reference numerals are given to those with the same functions, and repeated explanation thereof will be omitted.

First, the MRI apparatus related to the invention will be described on the basis of FIG. 1. FIG. 1 is a block diagram showing the overall configuration of an embodiment of the MRI apparatus related to the invention.

This MRI apparatus acquires a tomographic image of an object 101 using an NMR phenomenon. As shown in FIG. 1, the MRI apparatus is configured to include a static magnetic field generation magnet 102, a gradient magnetic field coil 103 and a gradient magnetic field power source 109, a transmission RF coil 104 and an RF transmission unit 110, a receiving RF coil 105 and a signal detection unit 106, a signal processing unit 107, a measurement control unit 111, an overall control unit 108, a display and operation unit 113, and a bed 112 on which the object 101 is carried and which takes the object 101 to the inside of the static magnetic field generation magnet 102.

The static magnetic field generation magnet 102 generates a uniform static magnetic field in a direction perpendicular to the body axis of the object 101 in the case of a vertical magnetic field method and in the body axis direction in the case of a horizontal magnetic field method. A permanent magnet type, a normal conducting type, or a superconducting type static magnetic field generator is disposed around the object 101.

The gradient magnetic field coil 103 is a coil wound in three axial directions of X, Y, and Z, which are the real space coordinate system (stationary coordinate system) of the MRI apparatus, and each gradient magnetic field coil is connected to the gradient magnetic field power source 109, which drives the gradient magnetic field coil, so that a current is supplied thereto. Specifically, the gradient magnetic field power source 109 of each gradient magnetic field coil is driven according to a command from the measurement control unit 111, which will be described later, and supplies a current to each gradient magnetic field coil. As a result, the gradient magnetic fields Gx, Gy, and Gz are generated in the three axial directions of X, Y, and Z, respectively.

At the time of imaging of the two-dimensional slice surface, a slice gradient magnetic field pulse (Gs) is applied in a direction perpendicular to the slice surface (cross section of imaging) so that a slice surface of the object 101 is set, and a phase encoding gradient magnetic field pulse (Gp) and a frequency encoding gradient (readout) magnetic field pulse (Gf) are applied in the two remaining directions, which are perpendicular to the slice surface and are also perpendicular to each other, so that the positional information in each direction is encoded in an NMR signal (echo signal).

The transmission RF coil 104 is a coil which irradiates the object 101 with an RF pulse, and is connected to an RF transmission unit 110 so that a high-frequency pulse current is supplied thereto. As a result, an NMR phenomenon is induced in nuclear spins of atoms which form body tissue of the object 101. Specifically, the RF transmission unit 110 is driven according to a command from the measurement control unit 111, which will be described later, to perform amplitude modulation of the high-frequency pulse. By supplying this amplified pulse to the transmission RF coil 104 disposed close to the object 101, the object 101 is irradiated with the RF pulse.

In addition, the amount of electromagnetic wave energy which is emitted from a transmission-side high frequency coil 14a and absorbed by the object 101 is detected by a SAR detection unit 116 into which a signal from the RF transmission unit 110 is input. Data of the detected amount of absorption is output to the measurement control unit 111 which will be described later. Details of the SAR detection unit 116 will be described later.

The receiving RF coil 105 is a coil which receives an echo signal emitted by the NMR phenomenon of the nuclear spins which form body tissue of the object 101, and is connected to the signal detection unit 106 so that the received echo signal is transmitted to the signal detection unit 106.

The signal detection unit 106 performs detection processing of the echo signal received by the receiving RF coil 105. Specifically, a response echo signal of the object 101 induced by the RF pulse irradiated from the RF transmission coil 104 is received in the receiving RF coil 105 disposed close to the object 101. The signal detection unit 106 amplifies the received echo signal according to the command from the measurement control unit 111 to be described later, divides it into two signals perpendicular to each other by quadrature phase detection, performs sampling of each signal by the predetermined number (for example, 128, 256, or 512), converts each sampling signal into the digital amount by A/D conversion, and transmits it to the signal processing unit 107 to be described later. Accordingly, the echo signal is acquired as time-series digital data (hereinafter, referred to as echo data) that includes a predetermined number of sampling data.

The signal processing unit 107 performs various kinds of processing on the echo data and transmits the processed echo data to the measurement control unit 111.

The measurement control unit 111 is a control unit that transmits various commands for echo data collection, which is necessary for reconstruction of a tomographic image of the object 101, mainly to the gradient magnetic field power source 109, the RF transmission unit 110, and the signal detection unit 106 in order to control them. Specifically, the measurement control unit 111 operates under the control of the overall control unit 108 to be described later, and controls the gradient magnetic field power source 109, the RF transmission unit 110, and the signal detection unit 106 on the basis of a predetermined pulse sequence to repeatedly execute the application of an RF pulse and a gradient magnetic field pulse to the object 101 and the detection of an echo signal from the object 101, and controls the collection of echo data necessary for reconstruction of an image in relation to an imaging region of the object 101. The echo data from the signal processing unit 107 is output to the overall control unit 108 by these controls.

The overall control unit 108 performs control of the measurement control unit 111 and control of various kinds of data processing and display, storage, and the like of the processing result, and is configured to include an arithmetic processing unit 114, which has a CPU and a memory, and a storage unit 115, such as an optical disc and a magnetic disk. Specifically, when the measurement control unit 111 is controlled to collect echo data and the echo data from the measurement control unit 111 is input, the arithmetic processing unit 114 stores the echo data in a region equivalent to the K space of the memory on the basis of the encoding information applied to the echo data. The echo data group stored in the region equivalent to the K space in the memory is also called K space data. In addition, the arithmetic processing unit 114 executes signal processing, processing for image reconstruction based on a Fourier transform, or the like on the K space data, and displays an image of the object 101 which is the result on the display and operation unit 113, which will be described later, and also records the image of the object 101 in the storage unit 115.

The display and operation unit 113 includes a display unit that displays the reconstructed image of the object 101 and an operating unit used to input various kinds of control information of the MRI apparatus or control information of processing performed by the overall control unit 108, such as a track ball, a mouse, and a keyboard. This operating unit is disposed close to the display unit, so that the operator controls various kinds of processing of the MRI apparatus interactively through the operating unit while observing the display unit.

Nuclides imaged by current MRI apparatuses, which are widely used clinically, have a hydrogen nucleus (proton) which is a main constituent material of the object. The morphology or functions of the head, abdomen, limbs, and the like of the human body are imaged in a two-dimensional or three-dimensional manner by performing imaging of the spatial distribution of the proton density or the information regarding the spatial distribution of the relaxation time of the excited state.

First Embodiment

Next, a first embodiment of the MRI apparatus and the SAR adjustment method of the invention will be described. In the present embodiment, when executing a protocol obtained by combining a plurality of pulse sequences, a temporal change in the predicted value of SAR (hereinafter, referred to as an "predicted SAR value") is graphically displayed corresponding to each of the plurality of pulse sequences which form the protocol. In addition, the operator may perform protocol editing, such as the exchange of pulse sequences and the insertion of waiting time, on this graph so that the predicted SAR value becomes less than the upper limit of SAR (hereinafter, referred to as an upper SAR limit).

The predicted SAR value means a predicted value of the amount of electromagnetic wave energy of RF pulses emitted to the object and absorbed by the object, such as the whole body SAR, the body part SAR, and the local SAR described above. The graph of the predicted SAR value (hereinafter, referred to as a SAR graph) is displayed according to one of these three types of SAR or a combination of the plurality of types of SAR.

Hereinafter, details of the present embodiment will be described using FIGS. 2 to 5.

Figure 2:
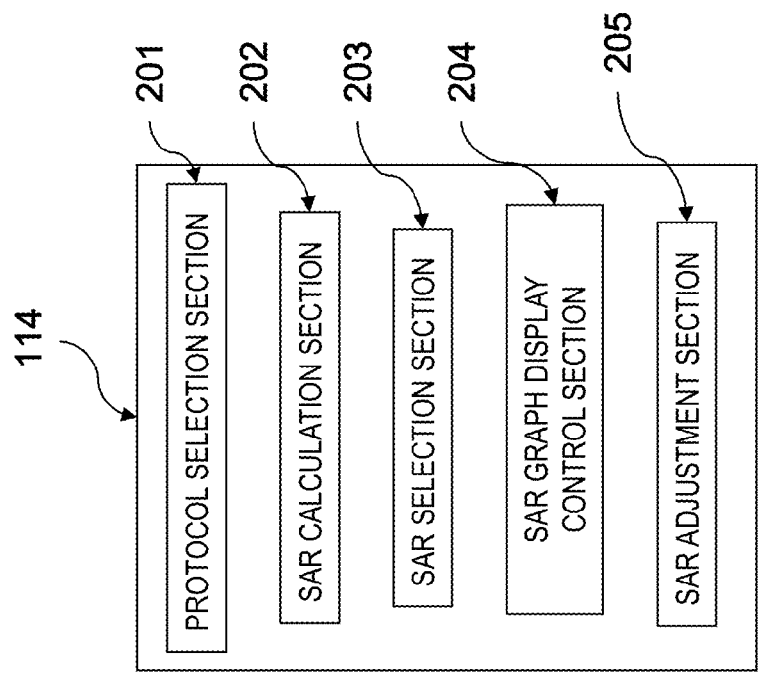
FIG. 2 is a functional block diagram showing each function of an arithmetic processing unit related to a first embodiment.

First, each function of arithmetic processing related to the present embodiment will be described on the basis of a functional block diagram of the arithmetic processing unit 114 shown in FIG. 2. The arithmetic processing unit 114 related to the present embodiment is configured to include a protocol selection section 201, a SAR calculation section 202, a SAR selection section 203, a SAR graph display control section 204, and a SAR adjustment section 205.

The protocol selection section 201 displays a plurality of protocols, which are stored in the storage unit 115 in advance, on the display unit and also reads from the storage unit 115 data of a protocol selected by the operator through the operating unit and stores the data in a memory of the arithmetic processing unit 114. Here, the protocol is an imaging procedure obtained by combining a plurality of pulse sequences determined according to the diagnostic purpose. The pulse sequence is an imaging method for acquiring a certain specific contrast. There are examples of a spin echo (SE) pulse sequence, a gradient echo (GrE) pulse sequence, an echo planar pulse sequence, a fast spin echo (FSE) pulse sequence, a Time-of-flight (TOF) pulse sequence. In addition, when the operator edits a protocol before imaging, processing of the protocol selection section 201 is not necessary.

The SAR calculation section 202 calculates the upper limit of SAR for each SAR type on the basis of object information (age, sex, weight, and the like) input in advance. In addition, the SAR calculation section 202 calculates a temporal change in the predicted SAR value of each pulse sequence for each SAR type on the basis of the imaging conditions of the respective pulse sequences, which form the protocol selected by the protocol selection section 201, and the execution order of the pulse sequences. The SAR type is one of the whole body SAR, the body part SAR, and the local SAR described above. These types of SAR also depend on the execution order of pulse sequences. Accordingly, as will be described later, when protocol editing such as the exchange of pulse sequences or the insertion of waiting time is performed, the SAR calculation section 202 recalculates a temporal change in the predicted SAR value for each pulse sequence.

The SAR selection section 203 compares the temporal change in the predicted value of each SAR type for each pulse sequence, which has been calculated by the SAR calculation section 202, with the upper SAR limit of each SAR type and selects the SAR type that requires attention. Here, the "SAR type that requires attention" means a SAR type in which the predicted SAR value is the same as or exceeds the upper SAR limit, or means a SAR type having a predicted SAR value close to the upper SAR limit when there is no such SAR type. When there is a plurality of "SAR types that require attention", these SAR types may be selected, or the largest SAR type exceeding the upper SAR limit or the SAR type closest to the upper SAR limit may be selected. In addition, the SAR selection section 203 specifies a pulse sequence having the "SAR type that requires attention" among the plurality of pulse sequences which form the protocol. When a plurality of pulse sequences have "SAR types that require attention", these plurality of pulse sequences are specified. In addition, the "SAR type that requires attention" may differ for each pulse sequence.

The SAR graph display control section 204 creates a SAR graph showing the temporal change in the predicted SAR value for the SAR type selected by the SAR selection section 203 and displays the SAR graph on the display unit. In addition, when displaying the SAR graph, the upper limit of the SAR type displayed graphically is displayed together.

For example, the SAR graph is expressed by plotting the predicted SAR value on the two-dimensional coordinates, in which the vertical axis indicates a predicted SAR value and the horizontal axis indicates elapsed time or a pulse sequence type, as a curve. When the pulse sequence type is set on the horizontal axis, the same horizontal axis as when the elapsed time is set on the horizontal axis can be made by setting the period width of each pulse sequence corresponding to the imaging time.

In addition, a background color in the SAR graph and a display mode of a predicted value curve, such as the line type, thickness, and color, may differ for each pulse sequence or waiting time so that the characteristics of each pulse sequence, which forms a protocol, and the relationship between the predicted SAR value and the upper SAR limit or the waiting time, which will be described later, can be clearly distinguished. For example, the display modes may be different in the following points of view.

(1) A pulse sequence with a predicted SAR value less than the upper SAR limit (hereinafter, referred to as a "pulse sequence less than the upper limit") and a pulse sequence equal to or greater than the upper SAR limit (that is, a pulse sequence which is the same as or exceeds the upper SAR limit) (hereinafter, referred to as an "excess pulse sequence") may be displayed in different display modes. For example, in the case of an FSE (fast spin echo) based pulse sequence, the predicted SAR value tends to exceed the upper SAR limit. In addition, a GrE (gradient echo) based pulse sequence tends to have a low SAR. Accordingly, these pulse sequences may be displayed in different modes.

(2) A pulse sequence which is movable in a protocol since the execution order can be changed (hereinafter, referred to as a "movable pulse sequence") and a pulse sequence which is not movable since the execution order cannot be changed (hereinafter, referred to as an "immovable pulse sequence") may be displayed in different display modes. For example, since positioning imaging is performed first, a pulse sequence for this is immovable. However, a pulse sequence after the positioning imaging is movable if there is no particular restriction. Accordingly, these pulse sequences may be displayed in different display modes.

(3) A waiting time region and other pulse sequence regions may be displayed in different display modes.

In addition, when a plurality of "SAR types that require attention" are selected by the SAR selection section 203 and graphs of these SAR types are displayed together, relative value display which shows the ratio of the predicted value to the upper limit of each SAR type or absolute value display which shows each predicted value as it is may be performed on the vertical axis of the SAR graph. In the case of relative value display, there is one line indicating the upper SAR limit. In the case of absolute value display, however, lines indicating the upper SAR limit are displayed as many as the displayed SAR types. How to display the graph of which SAR type may be set in advance or may be selected by the operator.

In addition, for SAR types that are graphically displayed as predicted SAR values, not only the predicted SAR value of the "SAR type that requires attention" but also the predicted SAR values of a plurality of SAR types may be graphically displayed simultaneously. Alternatively, predicted SAR values may be graphically displayed for one or a plurality of SAR types that the operator wants.

Figure 3:
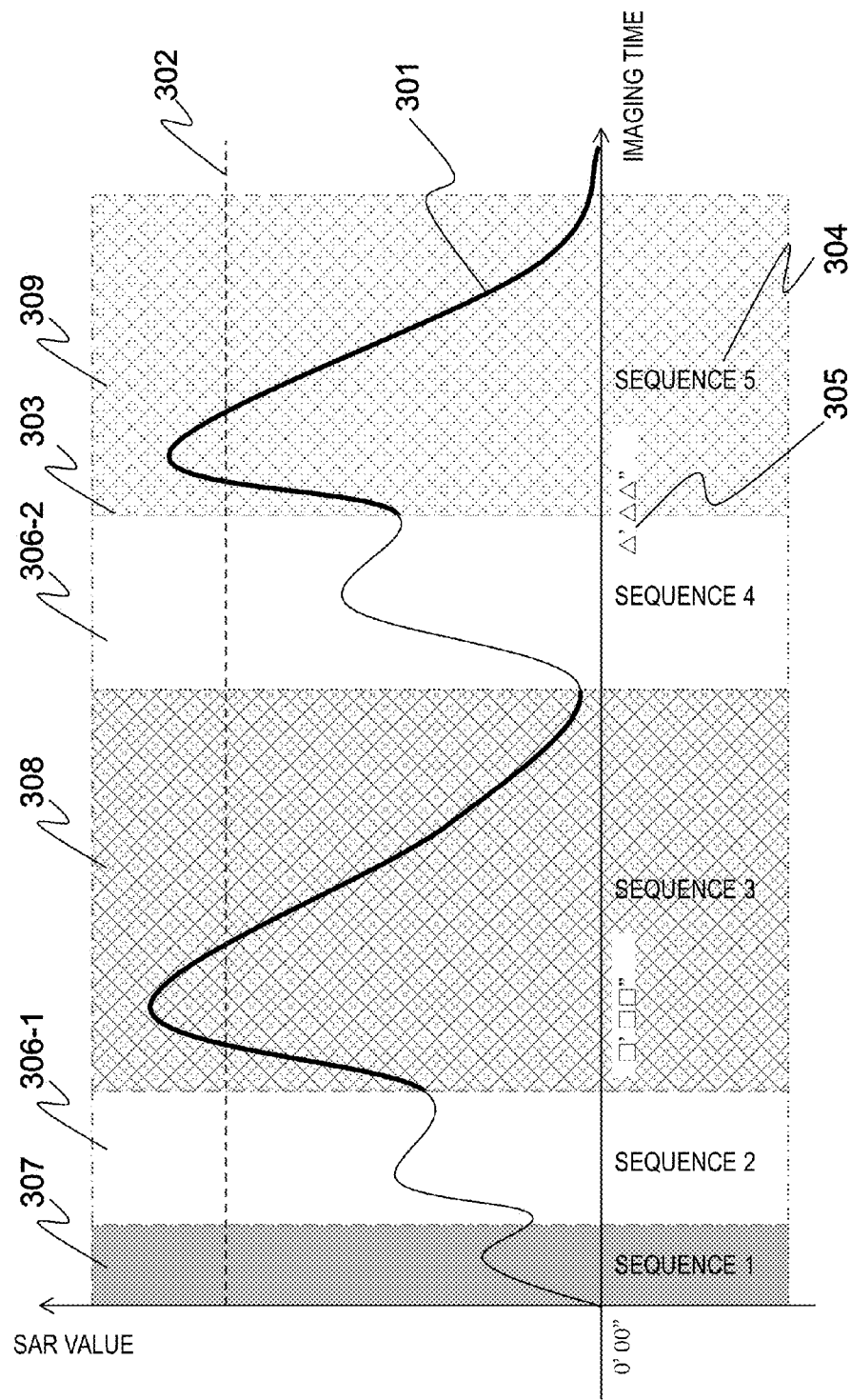
FIG. 3 is a view showing a SAR graph, which shows a temporal change in the predicted SAR value when executing a protocol obtained by combining five pulse sequences.

FIG. 3 shows an example of the SAR graph. FIG. 3 shows a SAR graph showing a temporal change in the predicted SAR value when executing the protocol obtained by combining five pulse sequences. Specifically, FIG. 3 is a SAR graph expressed by plotting the predicted value of the body part SAR on the two-dimensional coordinates in which the horizontal axis indicates imaging elapsed time or the type of the pulse sequence and the vertical axis indicates a SAR value. This body part SAR is the SAR type which is calculated by the SAR calculation section 202 on the basis of object information and the characteristics of the pulse sequence and is selected as the "SAR type that requires attention" by the SAR selection section 203. In addition, an upper limit 302 of the body part SAR is also displayed together with a time change curve 301 of the predicted value of the body part SAR. Since the upper limit 302 is a fixed value, the upper limit 302 is displayed as a line parallel to the horizontal axis.

In addition, a separation line 303 is displayed on the horizontal axis of the graph for each pulse sequence. In this case, a distance between two adjacent separation lines may be displayed corresponding to the imaging time of the pulse sequence therebetween. In addition, a pulse sequence name 304 and an imaging time 305 may be displayed for each pulse sequence.

In addition, the SAR graph in FIG. 3 shows an example of a method of different display modes. Specifically, the SAR graph in FIG. 3 is expressed by plotting the predicted SAR value on the white background color using a thin prediction curve for the body part SAR of a pulse sequence 306 (306-1 and 306-2) which is less than the upper limit and is movable, plotting the predicted SAR value on the gray background color using a thin prediction curve for the body part SAR of a pulse sequence 307 which is less than the upper limit and is immovable, plotting the predicted SAR value on the solid rhombic background using a thick prediction curve for the body part SAR of a pulse sequence 308 which exceeds the upper limit and is movable, and plotting the predicted SAR value on the dotted rhombic background using a thick prediction curve for the body part SAR of a pulse sequence 309 which exceeds the upper limit and is immovable.

The SAR adjustment section 205 performs protocol editing, such as the waiting time insertion or the exchange of a plurality of pulse sequences which form a protocol. When the predicted SAR value of one of the plurality of pulse sequences that form a protocol is the same as or exceeds the upper SAR limit, changing the execution order of each pulse sequence which forms the protocol or inserting the waiting time is the invention. In the present embodiment, an operator performs such a protocol editing operation on the SAR graph through the display and operation unit 113 (an exchange operation input unit or a waiting time inserting operation input unit). According to the operator's protocol editing operation, the SAR adjustment section 205 performs protocol editing, such as the exchange of pulse sequences or the waiting time insertion, to update the protocol data. In addition, whenever certain protocol editing is performed, the SAR calculation section 202 recalculates a temporal change in the predicted SAR value of each pulse sequence on the basis of the execution order of the respective pulse sequences, which form the edited protocol, for each SAR type (at least the selected SAR type). In addition, the SAR selection section 203 selects a SAR type that requires attention, and the SAR graph display control section 204 displays graphically the predicted SAR value for the selected SAR type. As a result, the SAR graph is updated.

Figure 4:
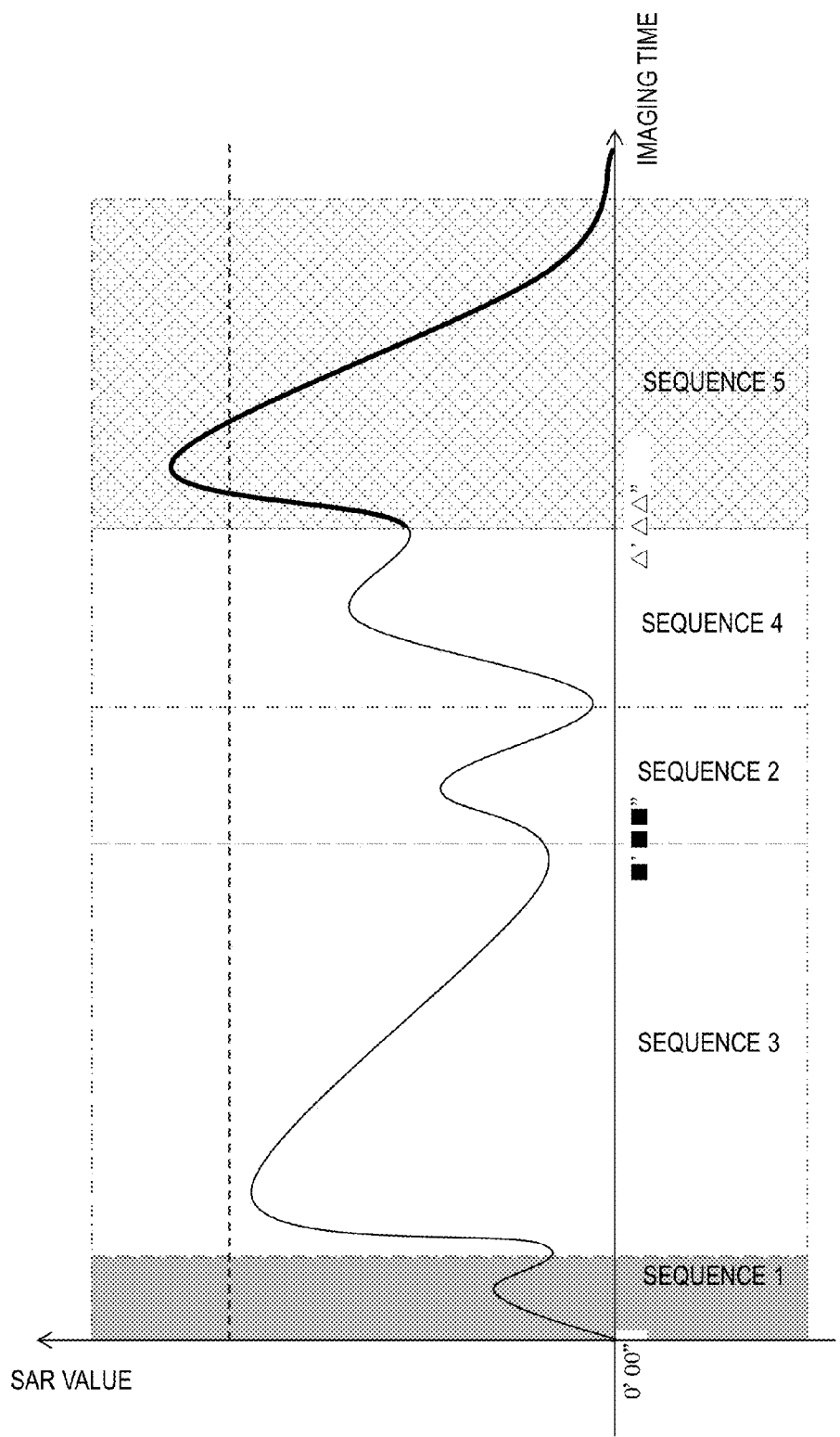
FIG. 4 is a view showing a SAR graph in which the order of pulse sequences 2 and 3 in FIG. 3 is changed and the predicted SAR values subsequent to the pulse sequence 3 after the exchange are recalculated.

For example, when the excess pulse sequence is a movable pulse sequence, it is possible to reduce the predicted SAR value by changing the position of the pulse sequence. When the SAR adjustment section 205 performs the exchange of pulse sequences on the basis of the operator's pulse sequence exchange operation on the SAR graph, the SAR calculation section 202 recalculates the predicted SAR values after the first exchanged pulse sequence for the same SAR type as the displayed SAR graph. In addition, the SAR graph display control section 204 displays the recalculated predicted SAR values graphically. As a result, the SAR graph is updated. FIG. 4 shows an example of the SAR graph after the exchange of the movable pulse sequence. In the example of FIG. 4, a case is shown in which the order of the pulse sequences 2 and 3 in FIG. 3 is changed and the predicted SAR values after the pulse sequence 3 after the exchange are recalculated and as a result, the predicted SAR value in the pulse sequence 3 which has exceeded the upper limit becomes less than the upper limit.

Figure 5:
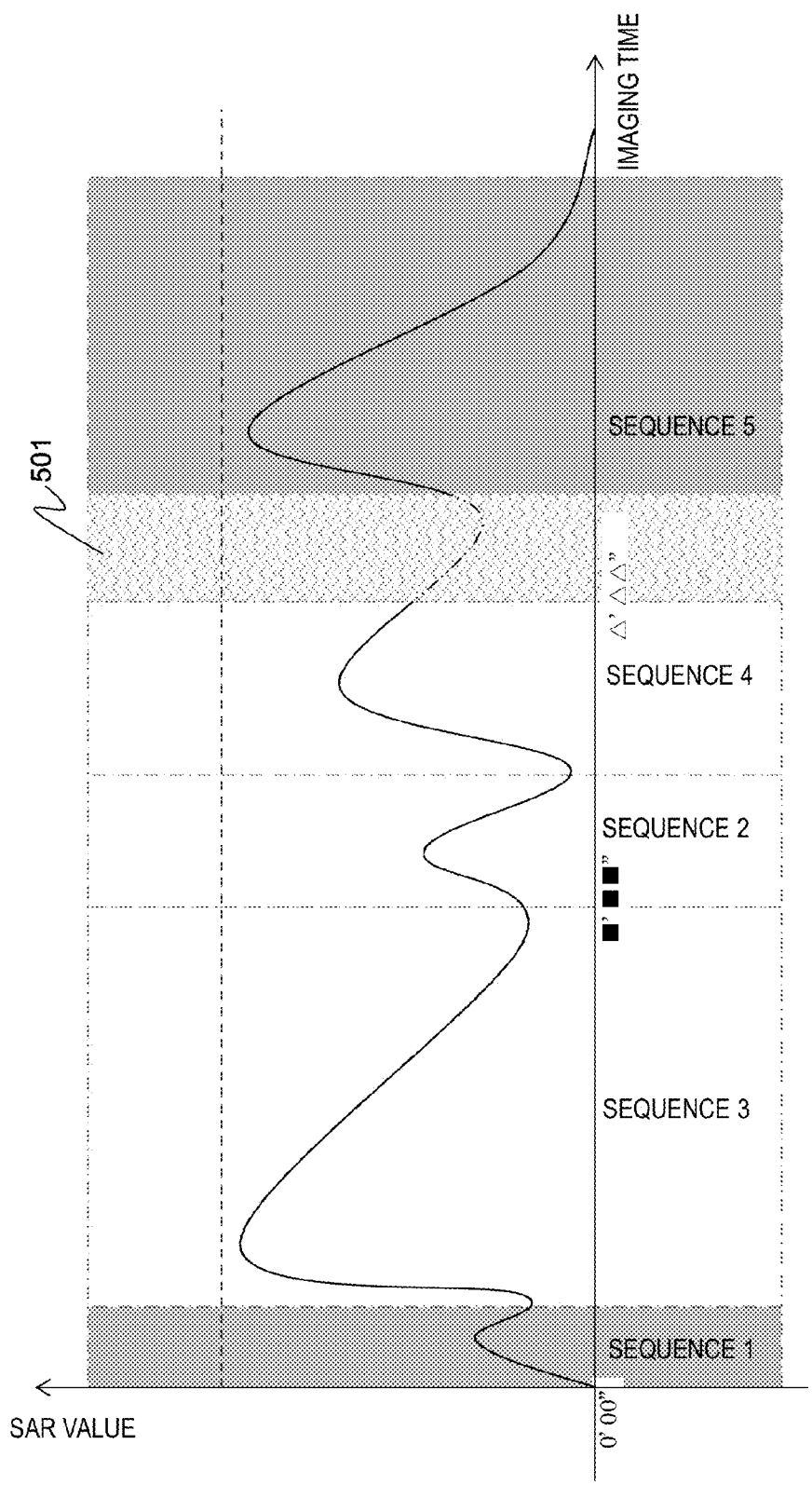
FIG. 5 is a view showing a SAR graph in which the predicted SAR values are recalculated after inserting a waiting time between pulse sequences 4 and 5 in FIG. 4.

In addition, when the excess pulse sequence is an immovable pulse sequence, it is possible to reduce the predicted SAR value by inserting the waiting time before the pulse sequence. On the basis of an operator's operation for waiting time insertion or an increase or decrease or deletion of the inserted waiting time on the SAR graph, the SAR adjustment section 205 inserts the waiting time between the pulse sequences and increases or decreases or deletes the inserted waiting time. Then, the SAR calculation section 202 recalculates the predicted SAR values after the insertion place for the same SAR type as the displayed SAR graph. In addition, the SAR graph display control section 204 displays the recalculated predicted SAR values graphically and sets the inserted waiting time region in a different display mode from other regions. As a result, the SAR graph is updated. FIG. 5 shows an example of the SAR graph after the waiting time insertion. In the example of FIG. 5, a case is shown in which the predicted SAR value of the pulse sequence 5 becomes less than the upper limit due to the insertion of the waiting time 501 between the pulse sequences 4 and 5 even though the predicted SAR value of the pulse sequence 5 in FIG. 4 still exceeds the upper limit. In addition, the inserted waiting time is displayed in a wavy line background pattern so as to have a different display mode from the other pulse sequence regions. In addition, also when the excess pulse sequence is a movable pulse sequence, it is possible to insert the waiting time.

Figure 6:
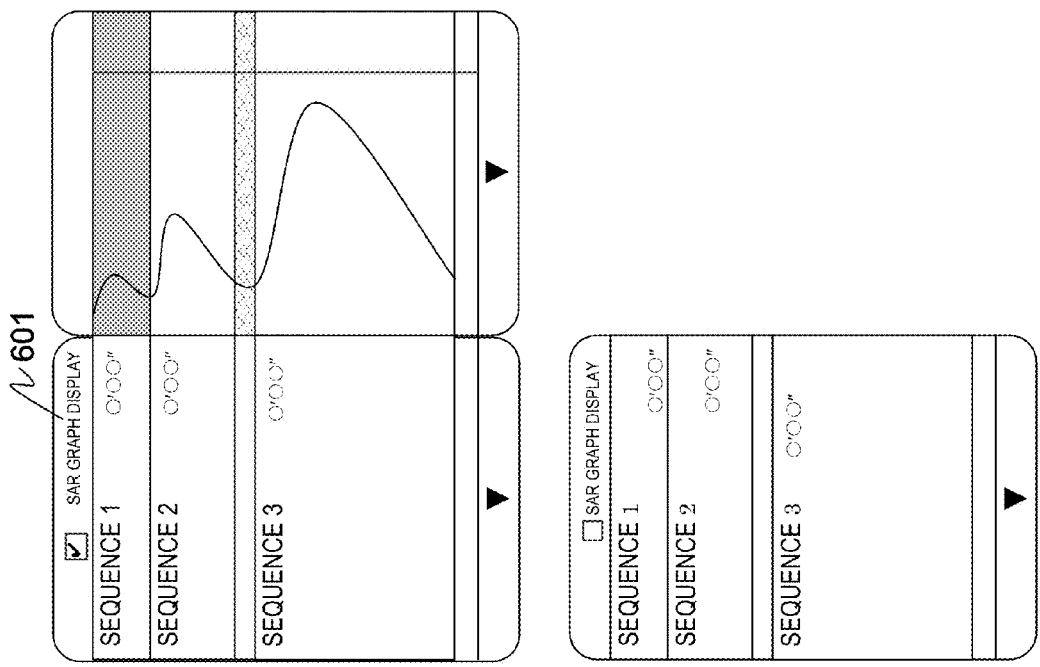
FIG. 6 is a view in which a SAR graph (right figure) and a protocol configuration diagram (left figure) are displayed in parallel so as to match the display width (time width) of each pulse sequence.

In addition, it is also possible to display each of the pulse sequences, which form a protocol, and the SAR graph so as to match each other. In addition, display/non-display of a SAR graph portion may be switched. FIG. 6 shows this example. FIG. 6 shows an example in which a SAR graph (right figure) and a protocol configuration diagram (left figure), which shows the respective pulse sequences that form a protocol in time series, are displayed in parallel so as to match the display width (time width) of each pulse sequence and switching of display/non-display of a SAR graph portion can be performed through a check box 601 provided at the protocol configuration diagram side. A protocol editing operation may be performed either on the protocol configuration diagram or on the SAR graph. In this case, the other side is simultaneously edited according to the editing operation performed on one side, and both the sides are redisplayed together.

The above pulse sequence exchange operation, waiting time inserting operation, and graphical display switching operation are performed by the operator through a track ball, a mouse, or a keyboard of the operating unit. With the track ball or the mouse, the above operations can be realized by the operation using a method of selection from the menu displayed on the display unit, a method of clicking a button, and a method of dragging the display item itself.

For example, in a head routine examination, a T1 weighted image, a T2 weighted image, a FLAIR image, a diffusion weighted image, an MRA image, and the like are imaged. The T1 weighted image or the T2 weighted image is generally imaged according to the SE sequence or the FSE sequence, and the predicted SAR value tends to become high. On the other hand, the MRA image is generally imaged according to the TOF sequence. Since this is a GrE based sequence, the predicted SAR value tends to become low. Therefore, there is a case where the predicted SAR value can be reduced by exchanging the imaging order of the T1 weighted image or the T2 weighted image and the MRA image without changing the imaging conditions.

Next, the process flow of the present embodiment performed by cooperation of the respective functional sections of the arithmetic processing unit 114 will be described on the basis of the flow chart shown in FIGS. 7A and 7B. This flow chart is stored in the storage unit 115 in advance as a program, and is executed when the program is loaded to the memory of the arithmetic processing unit 114 and is executed by a CPU or the like when necessary.

First, the entire process flow will be described on the basis of FIG. 7A.

In step S701, the operator inputs object information of height, weight, age, sex, and the like through the operating unit.

In step S702, the SAR calculation section 202 calculates an upper SAR limit for each SAR type on the basis of the object information input in step S701.

In step S703, the protocol selection section 201 displays a list of a plurality of protocols, which are stored in the storage unit 115 in advance, on the display unit in order to prompt the operator to select a desired protocol. The operator selects a desired protocol from the list and inputs or changes the imaging conditions of an imaging portion, an irradiation coil to be used, and the like according to the protocol selection. Alternatively, the operator may configure a protocol by inputting a plurality of pulse sequence and the imaging conditions of each pulse sequence, instead of selecting a protocol. In addition, the protocol selection section 201 reads the selected protocol data from the storage unit 115 and stores the protocol data in the memory of the arithmetic processing unit 114, or stores the data of the protocol configured by the operator in the memory of the arithmetic processing unit 114.

In step S704, SAR adjustment is performed. Details of the SAR adjustment will be described later.

In step S705, if the predicted SAR values for all pulse sequences which form the protocol are less than the upper SAR limit after the SAR adjustment in step S704, imaging is allowed. When the operator inputs the start of execution of imaging through the operating unit, the imaging is started.

Until now, the entire process flow of the present embodiment has been described.

Next, the detailed process flow of the above step S704 will be described on the basis of FIG. 7B.

In step S711, the SAR calculation section 202 calculates a temporal change in the predicted SAR value of each pulse sequence for each SAR type on the basis of the protocol and the imaging conditions input and set in step S703 and on the basis of the imaging conditions of the respective pulse sequences, which form the protocol, and the execution order of the pulse sequences. Then, the SAR selection section 203 selects a SAR type that requires attention from the calculated temporal change in the predicted SAR value for each SAR type.

In step S712, the SAR graph display control section 204 creates a SAR graph of the predicted SAR value of the selected SAR type and displays the SAR graph on the display unit. At the same time, the upper SAR limit calculated in step S702 is also displayed graphically. In this case, as described above, the SAR graph display control section 204 controls the display mode of each portion in the SAR graph, such as setting the display mode of the movable pulse sequence and the display mode of the immovable pulse sequence to be different from each other or setting the display mode of the excess pulse sequence and the display mode of the pulse sequence less than the upper limit to be different form each other.

In step S713, the SAR adjustment section 205 determines whether an excess pulse sequence having a predicted SAR value equal to or greater than the upper SAR limit is present or only pulse sequences less than the upper limit, which have predicted SAR values less than the upper SAR limit, are present. Then, when one pulse sequence exceeds the upper SAR limit (No), the SAR adjustment section 205 specifies the excess pulse sequence and proceeds to step S714. Only in the case of the pulse sequence less than the upper limit (Yes), the SAR adjustment ends.

In step S714, the SAR adjustment section 205 determines whether or not the excess pulse sequence specified in step S713 is movable. The process proceeds to step S715 when the excess pulse sequence specified in step S713 is movable (Yes), and the process proceeds to step S717 when the excess pulse sequence specified in step S713 is not movable (No).

In step S715, the operator performs a protocol editing operation to exchange the movable pulse sequences on the SAR graph through the operating unit when necessary. The SAR adjustment section 205 determines whether or not the operator has exchanged the movable pulse sequences. When the operator has exchanged the movable pulse sequences (Yes), the process proceeds to step S716. When the operator has not exchanged the movable pulse sequences (No), the process proceeds to step S717.

In step S716, the SAR adjustment section 205 determines a protocol reflecting the exchange of movable pulse sequences on the basis of the protocol editing operation to exchange the movable pulse sequences, which has been performed by the operator in step S715, and stores the determined protocol information in the memory. Then, the process returns to step S711 in which the predicted SAR values for the determined protocol is recalculated.

In step S717, the operator inserts a waiting time between the pulse sequences on the SAR graph through the operating unit when necessary. The SAR adjustment section 205 determines whether or not the operator has performed a waiting time insertion. When the operator has performed a waiting time insertion (Yes), the process proceeds to step S718. When the operator has not performed a waiting time insertion (No), the process returns to step S714 to repeat the monitoring of steps S715 and S717 until the operator performs either an operation to exchange the movable pulse sequences or an operation for the waiting time.

In step S718, the SAR adjustment section 205 determines a protocol reflecting the waiting time insertion on the basis of the protocol editing operation to insert the waiting time between the pulse sequences, which has been performed by the operator in step S717, and stores the determined protocol information in the memory. Then, the process returns to step S711 in which the predicted SAR values for the determined protocol is recalculated.

Until now, the detailed process flow of step S704 has been described.

As described above, according to the MRI apparatus and the SAR adjustment method of the present embodiment, a change in the predicted SAR value is graphically displayed corresponding to each of the plurality of pulse sequences which form a protocol. As a result, the operator can specify the pulse sequence equal to or greater than the upper SAR limit at a glance. In addition, the operator can perform a protocol editing operation, such as the exchange of pulse sequences or the waiting time insertion, on the SAR graph. As a result, when the predicted SAR value is equal to or greater than the upper SAR limit, it is possible to perform desired imaging within the restriction of the upper SAR limit without changing the imaging conditions input in advance.

Second Embodiment

Next, a second embodiment of the MRI apparatus and the SAR adjustment method of the invention will be described. A pulse sequence exchange program is prepared in the present embodiment. When the predicted SAR value of the pulse sequence is equal to or greater than the upper SAR limit, the apparatus performs an exchange of pulse sequences or a waiting time insertion automatically, thereby performing the re-editing of the protocol automatically. Hereinafter, only different parts from the above first embodiment will be described in detail, and explanation of the same part will be omitted.

For the pulse sequence exchange algorithm related to the present embodiment, it is possible to use the technique disclosed in PTL 3, for example. Here, detailed explanation of this algorithm will be omitted.

First, each function of arithmetic processing related to the present embodiment will be described on the basis of the functional block diagram of the arithmetic processing unit 114 shown in FIG. 2. The configuration of each functional section of the arithmetic processing unit 114 related to the present embodiment is the same as that in FIG. 2, but the content of processing of the SAR graph display control section 204 and the SAR adjustment section 205 is differ from that in the first embodiment.

The SAR adjustment section 205 reads and executes a program, which realizes the above-described pulse sequence exchange algorithm, from the storage unit 115 in which the program is stored in advance. When the predicted SAR value of any one of the plurality of pulse sequences which form a protocol is equal to or greater than (exceeds) the upper SAR limit, exchangeable pulse sequences are specified or the position (between the pulse sequences) at which the waiting time can be inserted is specified on the basis of the protocol information stored in the memory of the arithmetic processing unit 114. In addition, the content of processing is controlled by operator's selection from Automatic, Recommended display, Manual regarding pulse sequence exchange processing and waiting time insertion processing. If Automatic is selected, the SAR adjustment section 205 performs the pulse sequence exchange processing or the waiting time insertion processing automatically on the basis of the pulse sequence exchange algorithm. If Recommended display is selected, the exchange of the pulse sequences specified to be exchangeable or the insertion of waiting time specified to be able to be inserted is recommended to the operator. When the operator accepts these recommendations, this processing is performed. If Manual is selected, the same processing as in the first embodiment described above is performed.

In addition, when restrictions on pulse sequence exchange are designated in advance, the SAR adjustment section 205 performs the exchange according to the restriction information. A pulse sequence which cannot move is set as "movement prohibition". In addition, a group of a series of pulse sequences which cannot be separated from each other is set as "impossible separation". In addition, a plurality of groups of pulse sequences which cannot be separated from each other may be set. In this case, by setting the order of priority between groups, the order of priority is set as the order of the groups. In addition, the execution order of the pulse sequences included in a group may be changed within the group. For example, in a contrast examination, the T1 weighted image and the T2 weighted image are captured before and after injection of a contrast medium in many cases. Accordingly, a case may be considered in which each pulse sequence group is formed before and after injection of a contrast medium and the imaging order is changed within the group.

When Recommended display is selected, the SAR graph display control section 204 displays a SAR graph by changing the pulse sequence, which has been specified to be exchangeable by the SAR adjustment section 205, to have a different display mode from others. In this manner, the pulse sequence exchange is recommended to the operator. FIG. 8A shows an example of the display mode of exchangeable pulse sequences. In FIG. 8A, pulse sequences 2 and 3 are exchangeable, and each separation line of these pulse sequences is expressed as a thick dotted line 801. In addition, when there are no exchangeable pulse sequences, the SAR graph display control section 204 displays a SAR graph by changing a recommended waiting time insertion region to have a different display mode from others. FIG. 8B shows an example in which a waiting time region recommended to be inserted at the head position of the pulse sequence 5 is expressed with a thick dashed line 802.

Figure 9:
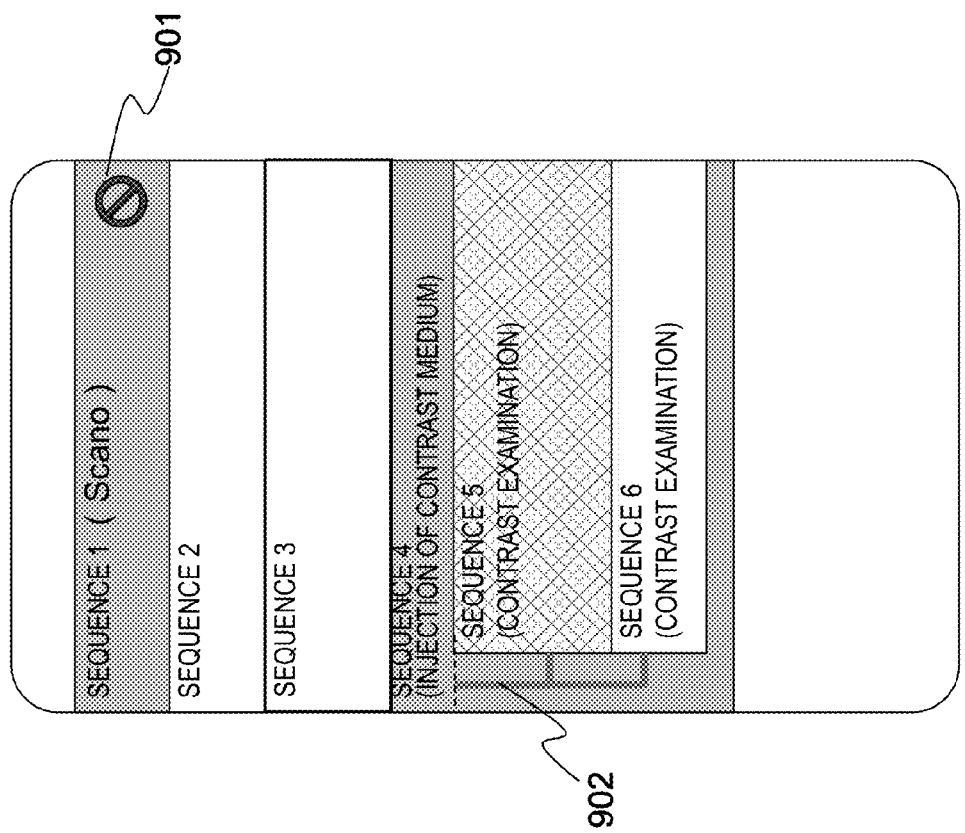
FIG. 9 is a view showing an example in which exchange restriction information is displayed on a protocol configuration diagram.

In addition, when exchange restriction information is set for pulse sequences, the SAR graph display control section 204 may display the exchange restriction information on the protocol configuration diagram shown in FIG. 6. FIG. 9 shows the example. A pulse sequence 1 is a preparatory scan for capturing or the like of a positioning image(scano image). Since the pulse sequence 1 needs to be performed first, a movement inhibition mark 901 is displayed in a region of the pulse sequence 1. In addition, pulse sequences 5 and 6 which are contrast examinations cannot be separated from a pulse sequence 4 in which a contrast medium is injected, and should always be executed after the pulse sequence 4. In this case, an inseparable pulse sequence group is formed by the pulse sequences 4, 5, and 6. In addition, when the predicted SAR value of the pulse sequence 5 is equal to or greater than the upper SAR limit, it is possible to exchange the pulse sequences 5 and 6. Therefore, an inseparable mark 902 is displayed in regions of the pulse sequences 4, 5, and 6. This inseparable mark 902 is a mark indicating the tree structure in which the pulse sequences 5 and 6 that can he exchanged hang down from the pulse sequence 4 that should be positioned at the head. Branch parts of this tree structure mark mean pulse sequences that can be exchanged.

Next, the process flow of the present embodiment performed by cooperation of the respective functional sections of the arithmetic processing unit 114 will be described on the basis of the flow chart shown in FIGS. 10A and 10B. In addition, detailed explanation regarding the same steps as in the flow chart of FIGS. 7A and 7B showing the process flow in the first embodiment described above will be omitted. This flow chart is stored in the storage unit 115 in advance as a program, and is executed when the program is loaded to the memory of the arithmetic processing unit 114 and is executed by a CPU or the like when necessary.

First, the entire process flow will be described on the basis of FIG. 10A.

Steps S701 to S703 are the same as the processing steps in the first embodiment shown in FIG. 7A. Accordingly, explanation of steps S701 to S703 will be omitted.

In step S1001, the operator selects a pulse sequence exchange method from "Automatic", "Recommended display", and "Manual". The SAR adjustment section 205 displays a menu shown in FIG. 11 on the display unit to receive the operator's selection. The operator selects and sets a desired method from "Automatic", "Recommended display", and "Manual" through the operating unit.

In step S1002, the operator may also set the order of priority of pulse sequence exchange or unexchangeable, or set a pulse sequence group. For example, <(group number)–(number in a group)>is set for each movable pulse sequence on the protocol configuration diagram shown in FIG. 9. The order of priority is set according to a group number, pulse sequences with the same group number are classified into the same group, and pulse sequences with the same number in a group are made to be exchangeable within a group. This step is skipped if these settings are not necessary.

In step S1003, the SAR adjustment section 204 determines the method selected in step 1001. When "Manual" is selected (Yes), the process proceeds to step S704 in order to adjust SAR manually. Since details of step S704 are the same as in the first embodiment described above, explanation thereof will be omitted. When a method other than "Manual", that is, "Automatic" or "Recommended display" is selected (No), the process proceeds to step S1004 in which automatic adjustment of SAR is performed on the basis of the setting in S1001 and S1002. Details of this step will be described later.

In step S705, if the predicted SAR values for all pulse sequences which form the protocol are less than the upper SAR limit after the SAR adjustment in step S704 or step S1004, imaging is allowed. When the operator inputs the start of execution of imaging through the operating unit, the imaging is started.

Until now, the entire process flow has been described.

Next, the detailed process flow of the above step S1004 will be described on the basis of FIG. 10B.

Since steps S711 to S714 are the same as the processing steps in the first embodiment shown in FIG. 7B, explanation of steps S711 to S714 and S718 will be omitted.

In step S1005, when a pulse sequence with a predicted SAR value equal to or greater than the upper SAR limit is movable (Yes in step S714), the SAR adjustment section 205 calculates a recommended exchange of pulse sequences. Then, when "Recommended display" is selected in step S1003, the SAR graph display control section 204 performs recommended display of the pulse sequence exchange on the SAR graph. This recommended display is the same as described above.

In step S1006, the SAR adjustment section 205 determines whether the selection in step S1003 is "Automatic" or "Recommended display". In the case of "Automatic", the process proceeds to step S710 in which the SAR adjustment section 205 executes the recommended exchange of pulse sequences calculated in step S1005. In the case of "Recommended display", the process proceeds to step S1007.

In step S1007, the SAR adjustment section 205 displays, for example, a confirmation message shown in FIG. 12(a) on the display unit in order for the operator to confirm whether or not the recommended exchange of pulse sequences calculated in step S1005 can be executed. Then, when the operator presses a "Yes" button to agree with the recommended exchange of pulse sequences (Yes), the process proceeds to step S710 in which the SAR adjustment section 205 executes the recommended exchange of pulse sequence calculated in step S1005. Then, the process returns to step S711 in which the predicted SAR value after the pulse sequence exchange is recalculated and the SAR graph is redisplayed. When the operator presses a "No" button to refuse the recommended exchange of pulse sequences (No), the process proceeds to step S1008.

In step S1008, when a pulse sequence with a predicted SAR value equal to or greater than the upper SAR limit is immovable (No in step S714) or when the operator presses a "No" button to refuse the recommended exchange of pulse sequences in step S1007, the SAR adjustment section 205 calculates a recommended waiting time insertion. Then, when "Recommended display" is selected in step S1003, the SAR graph display control section 204 performs recommended display of the waiting time insertion on the SAR graph. This recommended display is the same as described above.

In step S1009, the SAR adjustment section 205 determines whether the selection in step S1003 is "Automatic" or "Recommended display". In the case of "Automatic", the process proceeds to step S712 in which the SAR adjustment section 205 executes the recommended waiting time insertion calculated in step S1008. In the case of "Recommended display", the process proceeds to step S1010.

In step S1010, the SAR adjustment section 205 displays, for example, a confirmation message shown in FIG. 12(b) on the display unit in order for the operator to confirm whether or not the recommended waiting time insertion calculated in step S1008 can be executed. Then, the operator presses a "Yes" button to agree with the recommended waiting time insertion, the process proceeds to step S712 in which the SAR adjustment section 205 executes the recommended waiting time insertion calculated in step S1008. Then, the process returns to step S711 in which the predicted SAR value after the waiting time insertion is recalculated and the SAR graph is redisplayed. When the operator presses a "No" button to refuse the recommended waiting time insertion, the process returns to step S714.

The process in FIG. 10B is repeated until the exchange of pulse sequences or the insertion of waiting time is performed and the predicted SAR value becomes less than the upper SAR limit.

Until now, the detailed process flow of step S1004 has been described.

As described above, according to the MRI apparatus and the SAR adjustment method of the present embodiment, when the pulse sequence is equal to or greater than the upper SAR limit, the apparatus performs the re-editing of the protocol automatically by performing the exchanged of pulse sequences or the waiting time insertion automatically using the pulse sequence exchange algorithm. Therefore, since it is possible to reduce the burden on the operator's protocol re-editing, it is possible to perform desired imaging within the restriction of the upper SAR limit in a short time without changing the imaging conditions input in advance.

Third Embodiment

Next, a third embodiment of the MRI apparatus and the SAR adjustment method of the invention will be described. In the present embodiment, the exchange or the waiting time insertion for the non-executed pulse sequences is performed during the imaging based on a protocol. In this case, the observed value of SAR is measured, and the predicted SAR value and the SAR graph regarding the non-executed pulse sequence are updated on the basis of the observed SAR value that has been measured. Hereinafter, only different parts from the above first embodiment will be described in detail, and explanation of the same part will be omitted.

Figure 13:
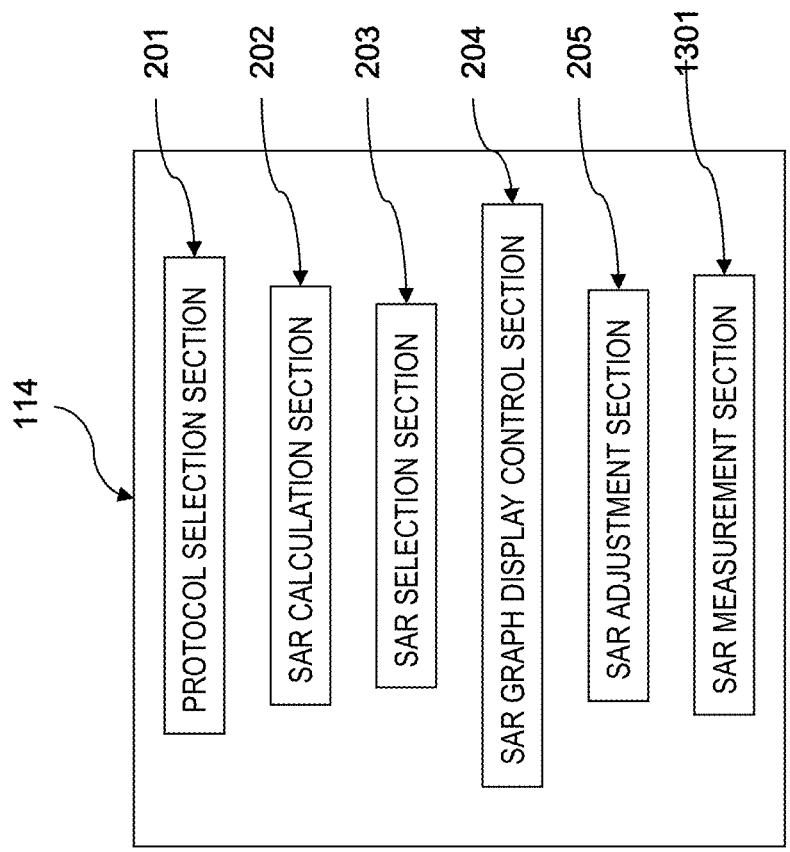
FIG. 13 is a functional block diagram showing each function of an arithmetic processing unit related to a third embodiment.

First, each function of arithmetic processing related to the present embodiment will be described on the basis of the functional block diagram of the arithmetic processing unit 114 shown in FIG. 13. The configuration of each functional section of the arithmetic processing unit 114 related to the present embodiment includes a SAR measurement section 1301 in addition to the configuration in the first embodiment shown in FIG. 2. In addition, the content of processing of the SAR calculation section 202, the SAR graph display control section 204, and the SAR adjustment section 205 is different from that in the first embodiment described above.

Figure 18:
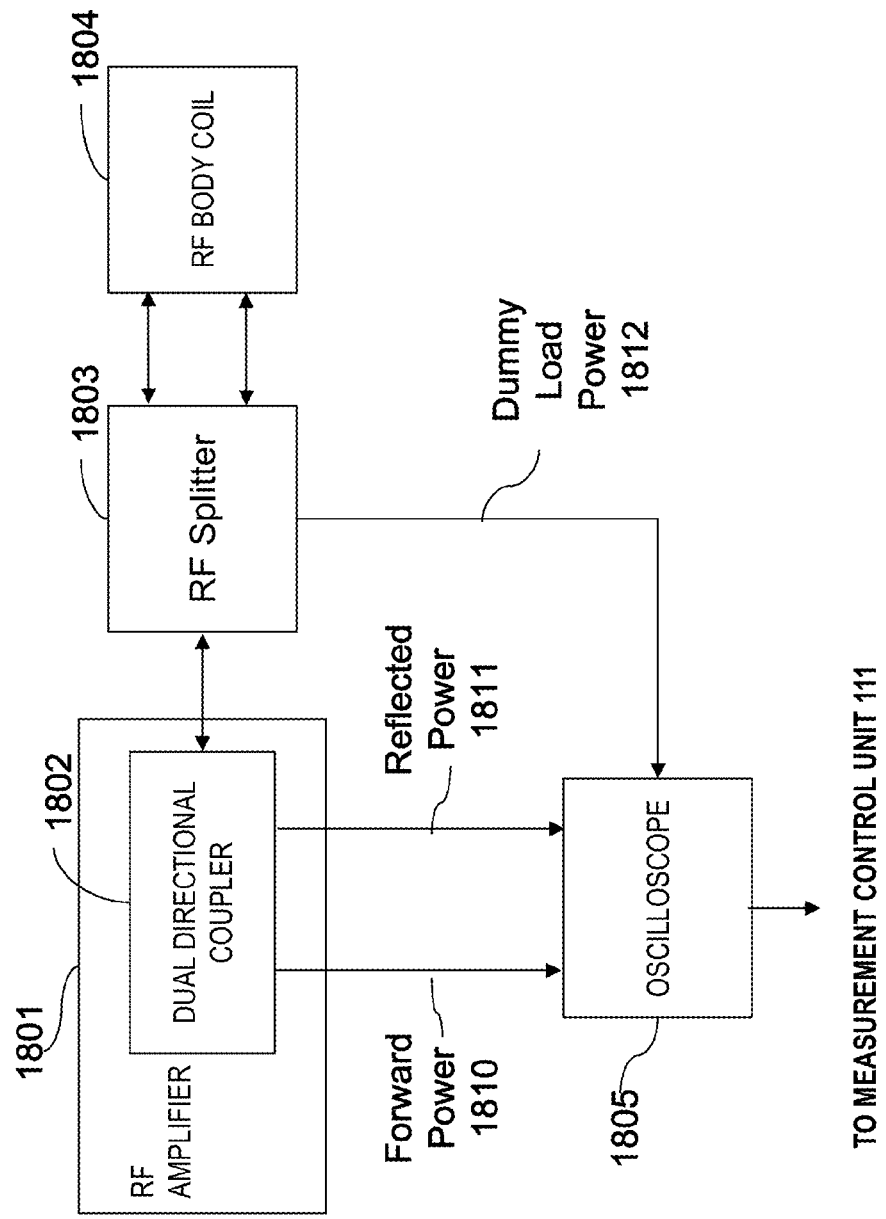
FIG. 18 is a view showing an example of a method of measuring the observed SAR value.

The method of measuring the observed SAR value is defined in advance in NEMA Standards Publication MS 8-2008. As shown in FIG. 18, the observed SAR value is measured by connecting an RF amplifier 1801 disposed in the RF transmission unit 110, a Dual directional coupler 1802 disposed in the RF amplifier 1801, an RF Splitter (which divides a high-frequency signal from the RF amplifier 1801 into 0° and 90° components) 1803, an RF Body coil 1804, and an oscilloscope 1805. The observed SAR value is a value obtained by dividing the peak power measured by the oscilloscope 1805 by the weight of the object. The peak power measured by the oscilloscope is calculated by the follow Expression.

$$P_{object} = P_{forward} - P_{reflect} - P_{dummy} - P_{coil} \quad (4)$$

$P_{forward}$ . . . Peak RF forward power flowing through a terminal of an RF coil (1810)

$P_{reflect}$ . . . Peak RF reflection power flowing through a terminal of an RF coil (1811)

$P_{dummy}$ . . . Power loss of a transmission circuit between a dummy load and an oscilloscope (1812)

$P_{coli}$ . . . Peak power absorbed by a no-load coil

In addition, the output of the oscilloscope 1805 is input to the SAR detection unit 116, or the peak RF forward power flowing through the terminal of the RF coil (1810), the peak RF reflection power flowing through the terminal of the RF coil (1811), and the power loss of the transmission circuit from the dummy load (1812) are input to the SAR detection unit 116 without passing through The oscilloscope 1805. In addition, the SAR detection unit 116 detects an envelope of each high-frequency signal, performs processing such as filtering or A/D conversion, and transmits the data after processing to the measurement control unit 111. The data input in the measurement control unit 111 is transmitted to the SAR measurement section 1301, and the SAR measurement section 1301 calculates the observed SAR value on the basis of these input values and the above-described Expression (4) when necessary or periodically and preferably, in real time.

The SAR calculation section 202 modifies the predicted SAR value of a non-executed portion (that is, a pulse sequence in which imaging has not yet started) on the basis of the observed SAR value of the executed portion (that is, a pulse sequence in which imaging has ended) in the protocol. For example, the SAR calculation section 202 modifies the predicted SAR value of a non-executed portion by calculating the ratio of the observed SAR value to the predicted SAR value of the executed portion, multiplying the predicted SAR value of the non-executed portion by the rate, and adding the result to the predicted SAR value of the executed portion. Since the protocol proceeds in real time, the observed SAR value is calculated according to the progress. Therefore, the SAR calculation section 202 updates the predicted SAR value of the non-executed portion in real time or appropriately.

Figure 14:
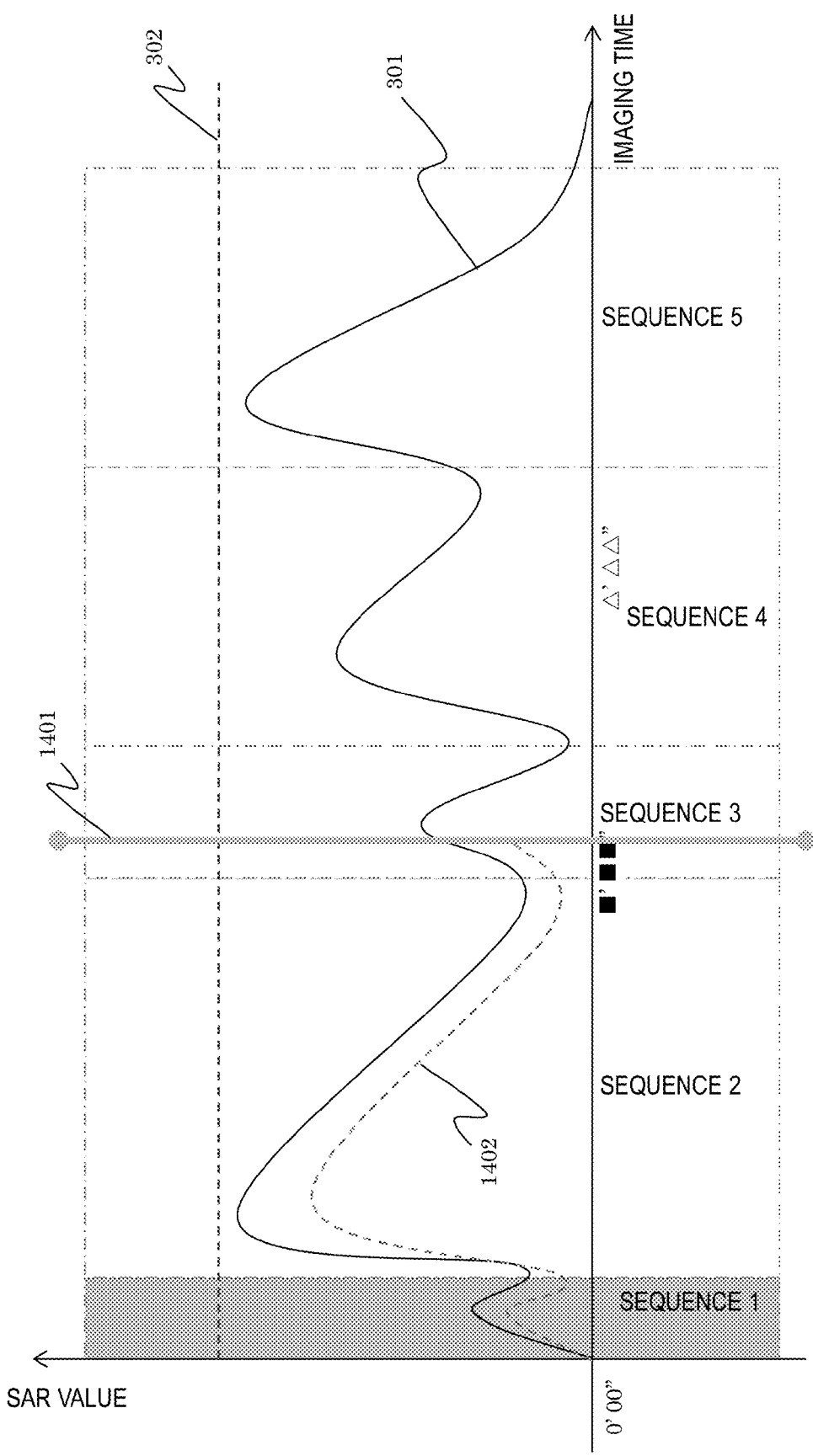
FIG. 14 is a view showing an example of the SAR graph which displays an observed SAR value with the progress of a protocol.

When displaying the SAR graph, the SAR graph display control section 204 displays not only the predicted SAR value but also the graph showing a change in the observed SAR value. In the case of graphical display of the observed SAR value, the observed SAR value is information added with the progress of the protocol. Accordingly, information or a mark indicating the progress situation of the protocol is also displayed on the SAR graph. In addition, the observed SAR value is displayed according to the change of the information or the mark indicating the progress situation of the protocol. In addition, the display of the observed SAR value may be performed appropriately (for example, every end of the pulse sequence) or may be performed in real time. On the other hand, in a non-executed portion of the protocol, when the predicted SAR value is modified on the basis of the observed SAR value of the executed portion of the protocol, the SAR graph display control section 204 updates the SAR graph so that the modification of the predicted SAR value is reflected on the graphical display. The update of the SAR graph may be performed appropriately (for example, every end of the pulse sequence) or may be performed in real time. FIG. 14 shows an example of the SAR graph which displays an observed SAR value with the progress of a protocol.

In the SAR graph shown in FIG. 14, the SAR graph display control section 204 moves a vertical line 1401, which is an example of information or a mark indicating the progress situation of a protocol, from the left side toward the right side with the progress of a protocol (that is, with the elapse of time). In addition, the SAR graph display control section 204 displays an observed SAR value curve 1402, which shows a temporal change in the observed SAR value, by plotting the observed SAR value at the left side of the vertical line on the SAR graph according to the movement of the vertical line 1401 (that is, according to the progress of the protocol). In addition, the SAR graph display control section 204 also displays a predicted SAR value curve 301 and an upper SAR limit line 302 on the SAR graph. Thus, a plurality of kinds of graphs are displayed on the SAR graph.

In addition, during the progress of the protocol, the operator may exchange the pulse sequences in a non-executed portion of the protocol or may insert, edit, and delete a waiting time in a non-executed portion. As an example, in FIG. 14, at the right side of the vertical line 1401 showing the current situation of the protocol progress, imaging has not yet been started in the pulse sequences 4 and 5. Accordingly, an operation of exchanging these pulse sequences is possible. In addition, it is also possible to insert, edit, and delete a waiting time before the pulse sequence 4 or 5. When the operation to exchange the pulse sequences or the operation to insert a waiting time has been performed, the SAR adjustment section 205 performs the re-editing of the protocol, the SAR calculation section 202 recalculates the predicted SAR value, and the SAR graph display control section 204 updates the SAR graph, for a non-executed portion of the re-edited protocol.

Figure 15:
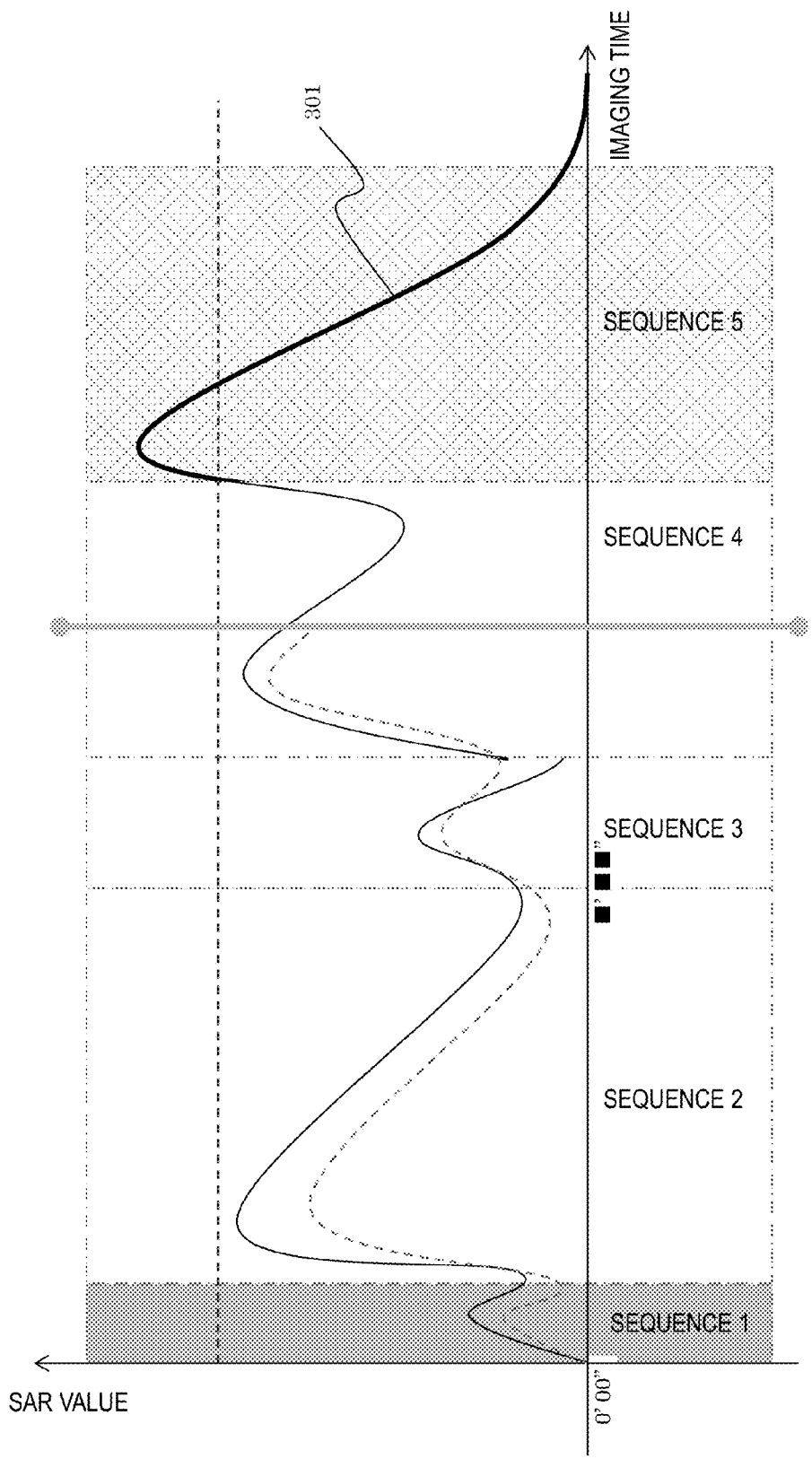
FIG. 15 is a view showing an example of the SAR graph before the waiting time is inserted during the progress of the protocol.
Figure 16:
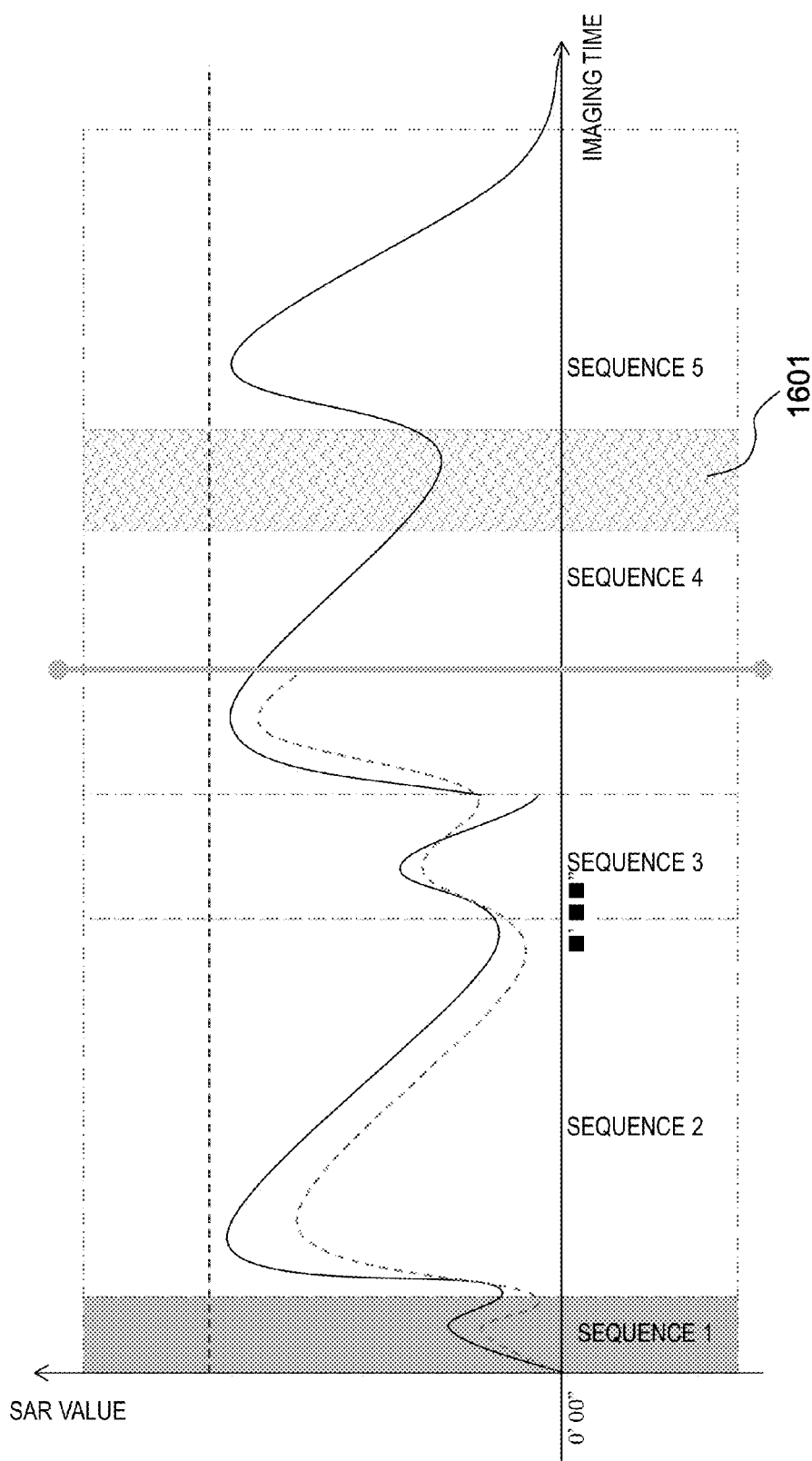
FIG. 16 is a view showing an example of the SAR graph after the waiting time is inserted during the progress of the protocol.

In addition, during the progress of the protocol, when the predicted SAR value recalculated on the basis of the observed SAR value is the same as or exceeds the upper SAR limit, the SAR adjustment section 205 inserts a waiting time. FIGS. 15 and 16 show examples of inserting a waiting time during the progress of the protocol. FIG. 15 shows a case in which, after the end of imaging of the pulse sequence 3, the SAR calculation section 202 recalculates the predicted SAR values of the pulse sequences 4 and 5 on the basis of the observed SAR values up to the pulse sequence 3 and the SAR graph display control section 204 updates a SAR graph on the basis of the recalculation result. FIG. 15 shows that, as a result of recalculation of the predicted SAR value, the recalculated predicted SAR value of the pulse sequence 5 exceeds the upper SAR limit and a part of the predicted SAR value curve 301 exceeds the upper SAR limit . In the case of FIG. 15, the pulse sequence 5 cannot be exchanged with other pulse sequences (is not movable) . Accordingly, the SAR adjustment section 205 inserts a waiting time before the pulse sequence 5, and the SAR graph display control section 204 updates the SAR graph so that the inserted waiting time is displayed. FIG. 16 shows an example of the SAR graph in which the waiting time 1601 is inserted before the pulse sequence 5. FIG. 16 shows that the predicted SAR value of the pulse sequence 5 has become less than the upper SAR limit by insertion of the waiting time 1601.

Figure 17:
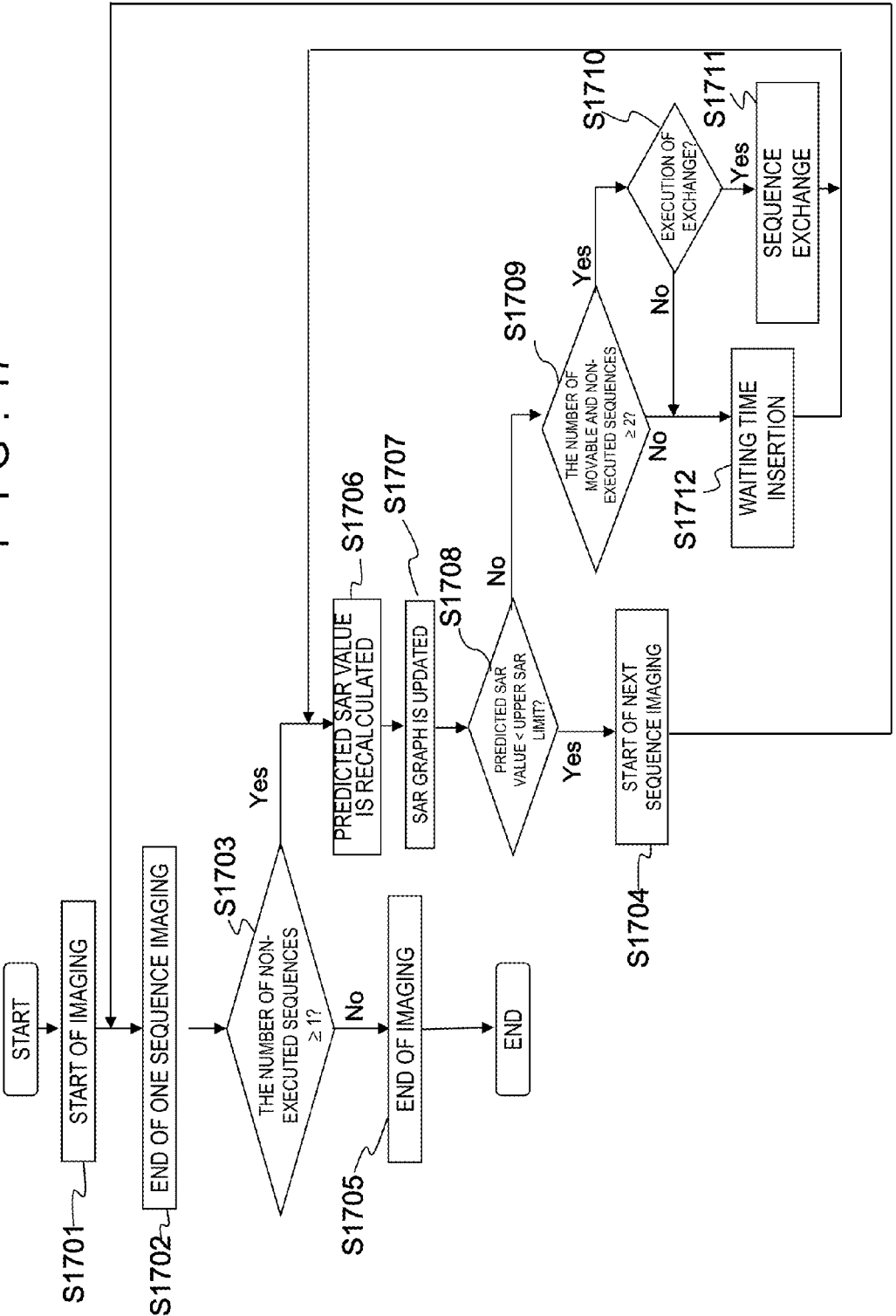
FIG. 17 is a view showing a flow chart, which shows the process flow of a third embodiment.

Next, the process flow of the present embodiment performed by cooperation of the respective functional sections of the arithmetic processing unit 114 will be described on the basis of the flow chart shown in FIG. 17. This flow chart is stored in the storage unit 115 in advance as a program, and is executed when the program is loaded to the memory of the arithmetic processing unit 114 and is executed by a CPU or the like when necessary.

In step S1701, the arithmetic processing unit 114 starts imaging according to a protocol. In this case, the arithmetic processing unit 114 instructs the measurement control unit 111 to execute each of a plurality of pulse sequences, which form the protocol, sequentially according to the execution order of the pulse sequences in the protocol. In addition, the SAR measurement section 1301 acquires an observed SAR value by measuring SAR in real time or appropriately according to the progress of the pulse sequence and stores the acquired observed SAR value in a memory of the arithmetic processing unit 114. In addition, the SAR graph display control section 204 displays information or a mark indicating the progress situation of the protocol on the SAR graph and also plots the observed SAR value on the SAR graph.

In step S1702, after the imaging of one pulse sequence in the protocol ends, the SAR measurement section 1301 counts non-executed pulse sequences in the protocol.

In step S1703, when the number of non-executed pulse sequences is 1 or more (Yes), the process proceeds to step S1706. When the number of non-executed pulse sequences is less than 1 (No), the process proceeds to step S1705.

In step S1705, when the number of non-executed pulse sequences is less than 1, imaging of all pulse sequences ends and the imaging based on the protocol ends accordingly.

In step S1706, the SAR calculation section 202 calculates the predicted SAR value of a non-executed pulse sequence in the protocol on the basis of the observed SAR value of the pulse sequence which is being executed or which has been executed. The method of calculation is the same as described above.

In step S1707, the SAR graph display control section 204 updates a non-executed pulse sequence portion in the protocol on the SAR graph on the basis of the predicted SAR value calculated in step S1706.

In step S1708, the SAR adjustment section 205 compares the predicted SAR value recalculated in step S1706 with the upper SAR limit. When the predicted SAR value is less than the upper SAR limit, the process proceeds to step S1704. When the predicted SAR value is equal to or greater than the upper SAR limit, the process proceeds to step S1709.

In step S1709, the SAR adjustment section 205 determines whether or not the number of non-executed pulse sequences is 2 or more and a movable pulse sequence is present in the non-executed pulse sequences. When this condition is satisfied (Yes), the process proceeds to step S1710. When this condition is not satisfied (No), the process proceeds to step S 1712.

In step S1710, in the non-executed portion of the protocol on the SAR graph, the operator performs a protocol editing operation to exchange the movable pulse sequences on the SAR graph through the operating unit when necessary. The SAR adjustment section 205 determines whether or not the operator has exchanged the movable pulse sequences. When the operator has exchanged the movable pulse sequences (Yes), the process proceeds to step S1711. When the operator has not exchanged the movable pulse sequences (No), the process proceeds to step S1712.

In step S1711, the SAR adjustment section 205 determines a protocol reflecting the exchange of movable pulse sequences on the basis of the protocol editing operation to exchange the movable pulse sequences, which has been performed by the operator in step S1710, and stores the determined protocol information in the memory. Then, the process proceeds to step S1706 in which recalculation of the predicted SAR value and updating of the SAR graph are performed.

In step S1712, the SAR adjustment section 205 inserts a waiting time in a non-executed portion of the protocol on the SAR graph. The waiting time is inserted at the head of one of non-executed pulse sequences. Then, the process proceeds to step S1706 in which recalculation of the predicted SAR value and updating of the SAR graph are performed.

In step S1704, when the predicted SAR value is less than the upper SAR limit in step S1708, the arithmetic processing unit 114 instructs the measurement control unit 111 to start the following pulse sequence. Then, the process proceeds to step S1702.

Until now, the entire process flow of the present embodiment has been described.

As described above, according to the MRI apparatus and the SAR adjustment method of the present embodiment, during the imaging based on the protocol, the observed value of SAR is measured for the pulse sequence which is being executed or which has been executed, and the predicted SAR value and the SAR graph regarding the non-executed pulse sequence are updated on the basis of the observed SAR value that has been measured. In addition, the operator can perform a protocol editing operation, such as the exchange or the waiting time insertion for the non-executed pulse sequences, on the graph. In this manner, it is possible to calculate the predicted SAR value more accurately. Accordingly, even if the predicted SAR value becomes equal to or greater than the upper SAR limit during the progress of the protocol, it is possible to perform desired imaging within the restriction of the upper SAR limit without changing the imaging conditions input in advance by performing the exchange or the waiting time insertion for the non-executed pulse sequences immediately.

Fourth Embodiment

Next, a fourth embodiment of the MRI apparatus and the SAR adjustment method of the invention will be described. In the present embodiment, it is possible to change various parameters of a pulse sequence on the SAR graph. Hereinafter, only different parts from the above first embodiment will be described in detail, and explanation of the same part will be omitted.

When there is no movable pulse sequence or when the predicted SAR value does not still become less than the upper SAR limit even if pulse sequences are exchanged and when the insertion of waiting time is not preferable, the execution of imaging becomes possible by changing various imaging parameters of the pulse sequence in a range that fits the purpose of the imaging. The present embodiment makes such a change of the imaging parameter possible on the SAR graph.

First, each function of arithmetic processing related to the present embodiment will be described on the basis of the functional block diagram of the arithmetic processing unit 114 shown in FIG. 19. The configuration of each functional section of the arithmetic processing unit 114 related to the present embodiment includes an imaging parameter setting section 1901 in addition to the configuration in the first embodiment shown in FIG. 2. In addition, the content of processing of the SAR calculation section 202 and the SAR graph display control section 204 is different from that in the first embodiment described above.

The imaging parameter setting section 1901 calculates a recommended value or a recommended range, which can reduce the predicted SAR value, for an imaging parameter that can be changed. In addition, when an instruction to change the imaging parameter value is input by the operator, the imaging parameter setting section 1901 changes the pulse sequence on the basis of the changed value of the imaging parameter and notifies the measurement control unit 111 of the changed pulse sequence information.

The SAR calculation section 202 recalculates the predicted SAR value for the pulse sequence for which the value of the imaging parameter has been changed.

The SAR graph display control section 204 displays a recommended range, which can reduce the current value and the predicted SAR value of the changeable imaging parameter calculated by the imaging parameter setting section 1901, on the SAR graph to receive an operator's instruction to change the imaging parameter value. In addition, the SAR graph display control section 204 updates the SAR graph on the basis of the predicted SAR value recalculated by the SAR calculation section 202.

Figure 20:
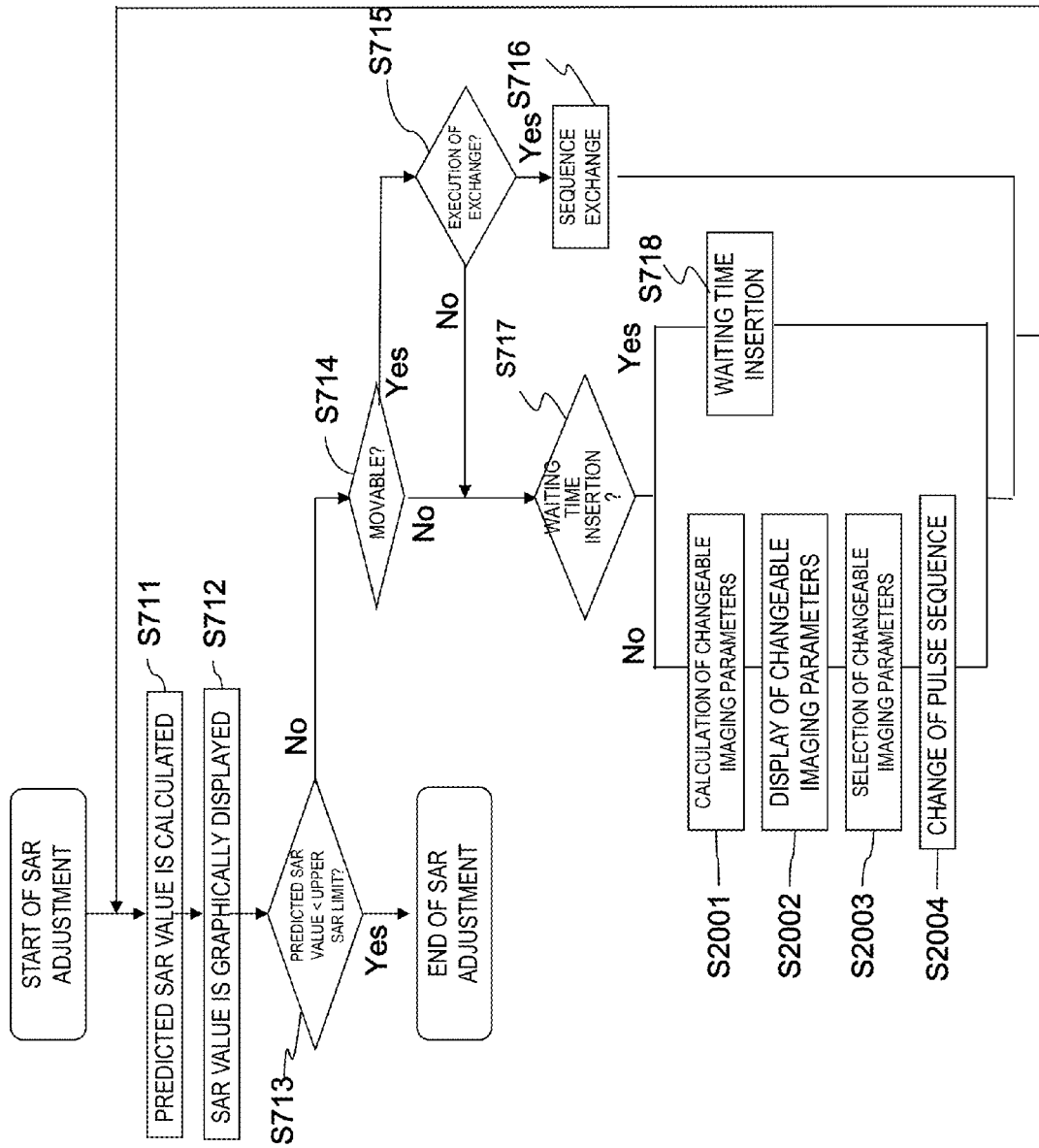
FIG. 20 is a view showing a flow chart, which shows the process flow of a fourth embodiment.

Next, the process flow of the present embodiment performed by cooperation of the respective functional sections of the arithmetic processing unit 114 will be described. Since the entire process flow of the present embodiment is the same as that in FIG. 7A, explanation thereof will be omitted. Details of step 5704 in the present embodiment will be described on the basis of the flow chart shown in FIG. 20. Only steps S2001 to S2004 in the flow chart of FIG. 20 are different from the flow chart in the first embodiment described in FIG. 7B. Since others are the same, explanation thereof will be omitted.

In step S2001, when there is no movable pulse sequence in a protocol (No in step S714) and the waiting time insertion is not possible (or there is no waiting time insertion; No in step S717), the imaging parameter setting section 1901 calculates a recommended value or a recommended range, which can reduce the predicted SAR value, for an imaging parameter that can be changed.

Figure 21:
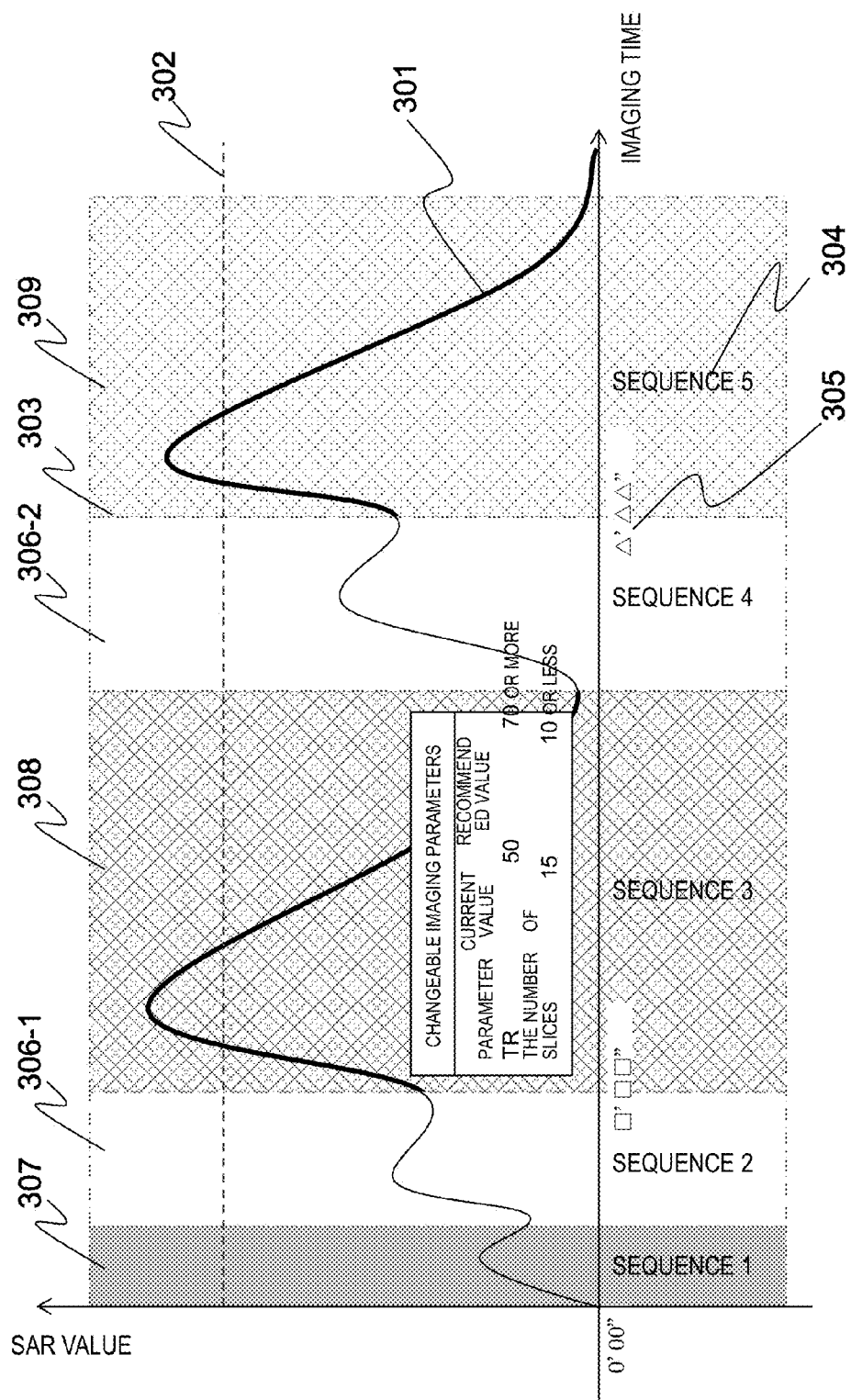
FIG. 21 is a view showing an example where changeable imaging parameters and recommended values, which can reduce the current values and the predicted SAR values of the imaging parameters, are displayed especially in a region of the excess pulse sequence within the SAR graph shown in FIG. 3.

In step S2002, the imaging parameter setting section 1901 displays a recommended value or a recommended range, which can reduce the current value and the predicted SAR value of the changeable imaging parameter, on the SAR graph. FIG. 21 shows an example of the display. FIG. 21 is an example where a TR (repetition time) and the number of slices, which are calculated as imaging parameters that can be changed, are selected especially in a region of the excess pulse sequence 3 within the SAR graph shown in FIG. 3, in which the predicted SAR value is equal to or greater than the upper SAR limit, and recommended values that can reduce the current values and the predicted SAR values of these imaging parameters are displayed.

In step S2003, for the imaging parameters that can be changed on the SAR graph, the operator selects and sets the values from the recommended range through the operating unit.

In step S2004, the imaging parameter setting section 1901 changes the pulse sequence on the basis of the values of the imaging parameters changed in step S2003 and notifies the measurement control unit 111 of the changed pulse sequence information. Then, the process proceeds to step S711 in which recalculation of the predicted SAR value and updating of the SAR graph are performed.

Figure 22:
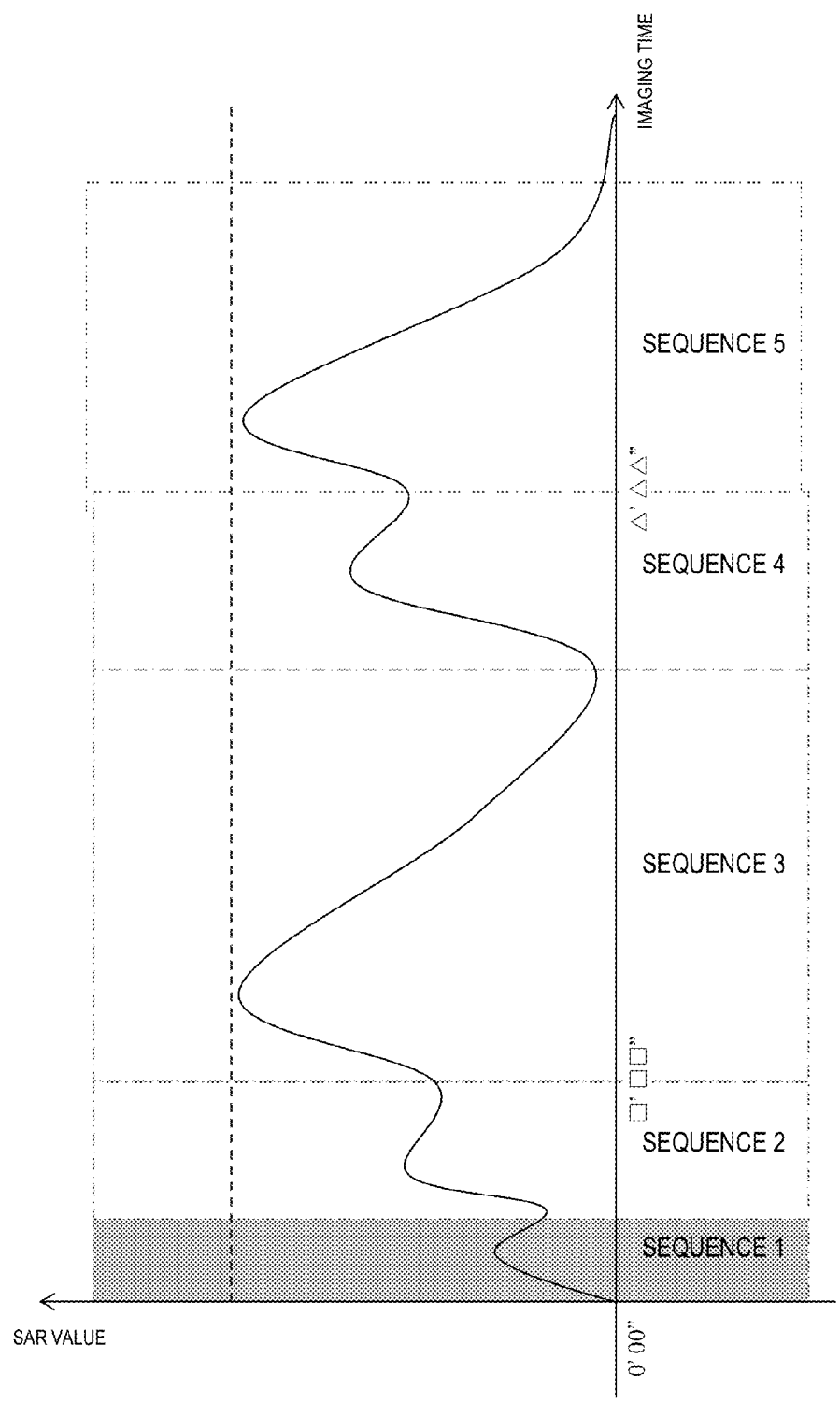
FIG. 22 is a view showing an example of the SAR graph after the imaging parameter values are changed.

By repeating the above process for all pulse sequences which form the protocol until the predicted SAR value becomes less than the upper SAR limit, it is possible to set the imaging parameter values that can be executed for all of the pulse sequences. As a result, the SAR graph, in which the predicted SAR value exceeding the upper SAR limit shown in FIG. 21 is present, changes to a graph shown in FIG. 22 in which all predicted SAR values are less than the upper SAR limit.

Until now, the entire process flow has been described.

Moreover, in the above explanation, an example of changing the values of the imaging parameters for the excess pulse sequence has been described. However, also for a pulse sequence less than the upper limit, the imaging parameter values may be changed when necessary.

In addition, the change of the imaging parameter values in the present embodiment may be performed before the start of the protocol as in the first embodiment or may be performed during the execution of the protocol as in the third embodiment.

As described above, according to the MRI apparatus and the SAR adjustment method of the present embodiment, it is possible to change various parameters of a pulse sequence on the SAR graph. In particular, when there is no movable pulse sequence in a protocol and it is not possible to insert a waiting time, the imaging parameter values can be changed. Therefore, also for a protocol or a pulse sequence that cannot be executed with the imaging conditions (imaging parameter values) set in advance, it is possible to execute desired imaging within the restriction of the upper SAR limit by changing the imaging parameter values in a possible range.

The above is specific embodiments to which the invention is applied. However, the invention is not limited to the content disclosed in each of the above embodiments, and various embodiments based on the spirit of the invention may be adopted. For example, the second and third embodiments may be combined so that, when the predicted SAR value of a non-executed portion of a protocol has become equal to or greater than the upper SAR limit during the progress of the protocol, the exchange or the waiting time insertion may be automatically performed for the pulse sequence of the non-executed portion.

REFERENCE SIGNS LIST

101: object
102: static magnetic field generation magnet
103: gradient magnetic field coil
104: transmission RF coil
105: receiving RF coil
106: signal detection unit
107: signal processing unit
108: overall control unit
109: gradient magnetic field power source
110: RF transmission unit
111: measurement control unit
112: bed
113: display and operation unit
114: arithmetic processing unit
115: storage unit
116: SAR detection unit

The invention claimed is:
1. A magnetic resonance imaging apparatus comprising:
an RF pulse control unit configured to control emission of an RF pulse to an object in imaging of the object performed by combination of a plurality of pulse sequences;

a Specific Absorption Rate (SAR) calculation unit configured to calculate a predicted SAR value which is a predicted value of electromagnetic wave energy absorbed by the object by the emission of the RF pulse, wherein the SAR calculation unit is further configured to calculate a temporal change in the predicted SAR value of each of the pulse sequences;

a SAR adjustment unit configured to adjust execution of the plurality of pulse sequences such that the predicted SAR value becomes less than an upper SAR limit;

a display unit configured to display the predicted SAR value; and a SAR graph display control unit configured to create a SAR graph showing the temporal change in the predicted SAR value of each of the pulse sequences and configured to display the SAR graph on the display unit, wherein the SAR graph display control unit is further configured to make a display mode of a movable pulse sequence, for which an execution order can be changed, and a display mode of an immovable pulse sequence, for which an execution order cannot be changed, different on the displayed SAR graph.

2. The magnetic resonance imaging apparatus according to claim 1, wherein the SAR graph display control unit displays a graph of the predicted SAR value showing the temporal change in the predicted SAR value of each of the pulse sequences and the upper SAR limit on the SAR graph.

3. The magnetic resonance imaging apparatus according to claim 2, wherein the SAR graph display control unit is further configured to display information, which shows a separation between the pulse sequences, on the SAR graph.

4. The magnetic resonance imaging apparatus according to claim 2, wherein the SAR graph display control unit is further configured to display a name and an imaging time of each of the pulse sequences, on the SAR graph.

5. The magnetic resonance imaging apparatus according to claim 1, wherein the SAR graph display control unit makes a display mode of a pulse sequence, in which the predicted SAR value is equal to or greater than the upper SAR limit, and a display mode of a pulse sequence, in which the predicted SAR value is less than the upper SAR limit, different on the SAR graph.

6. The magnetic resonance imaging apparatus according to claim 5, wherein the SAR graph display control unit makes a display mode of a background of the pulse sequence, in which the predicted SAR value is equal to or greater than the upper SAR limit, and a display mode of a background of the pulse sequence, in which the predicted SAR value is less than the upper SAR limit, different on the SAR graph.

7. The magnetic resonance imaging apparatus according to claim 1, further comprising:
an exchange operation input unit configured to receive an operation to exchange movable pulse sequences,
wherein the SAR graph display control unit updates the SAR graph after the pulse sequence exchange and displays the updated SAR graph on the display unit.

8. The magnetic resonance imaging apparatus according to claim 1, further comprising:
a waiting time inserting operation input unit configured to receive an operation to insert a waiting time between two pulse sequences,
wherein the SAR graph display control unit updates the SAR graph after the waiting time insertion and displays the updated SAR graph on the display unit.

9. The magnetic resonance imaging apparatus according to claim 1, wherein the SAR adjustment unit is further configured to specify movable pulse sequences and exchanges the specified pulse sequences.

10. The magnetic resonance imaging apparatus according to claim 1, wherein the SAR adjustment unit is further configured to specify a place where insertion of a waiting time between some of the plurality of pulse sequences is possible and inserts a waiting time at the specified place.

11. The magnetic resonance imaging apparatus according to claim 1, wherein the SAR graph display control unit is further configured to display information, which shows progress of imaging based on a combination of the plurality of pulse sequences, on the SAR graph.

12. The magnetic resonance imaging apparatus according to claim 1, further comprising:
a SAR measurement unit configured to calculate an observed SAR value which is electromagnetic wave energy absorbed by the object, for an executed pulse sequence or a pulse sequence under execution among the plurality of pulse sequences.

13. The magnetic resonance imaging apparatus according to claim 12, wherein the SAR graph display control unit is further configured to display a temporal change in the observed SAR value on the SAR graph.

14. The magnetic resonance imaging apparatus according to claim 12, wherein the SAR calculation unit is further configured to update a predicted SAR value for a non-executed pulse sequence among the plurality of pulse sequences on the basis of the observed SAR value, and
the SAR graph display control unit is further configured to update the SAR graph so that the updated predicted SAR value is reflected.

15. The magnetic resonance imaging apparatus according to claim 12, wherein the SAR adjustment unit is further configured to perform exchange of movable pulse sequences or insertion of a waiting time for a non-executed pulse sequence among the plurality of pulse sequences.

16. The magnetic resonance imaging apparatus according to claim 1, further comprising:
an imaging parameter setting unit configured to calculate a changeable imaging parameter wherein the predicted SAR value becomes less than the upper SAR limit for an imaging parameter of a pulse sequence with the predicted SAR value equal to or greater than the upper SAR limit,
wherein the SAR graph display control unit is further configured to display the changeable imaging parameter on the SAR graph.

17. The magnetic resonance imaging apparatus according to claim 16, wherein the SAR calculation unit is further configured to recalculate a predicted SAR value of a pulse sequence, in which the predicted SAR value becomes equal to or greater than the upper SAR limit, on the basis of a change of a value of the changeable imaging parameter, and
the SAR graph display control unit is further configured to update the SAR graph so that the recalculated predicted SAR value is reflected.

18. A Specific Absorption Rate (SAR) adjustment method in imaging of an object performed by combination of a plurality of pulse sequences in a magnetic resonance imaging (MRI) system, comprising:
calculating a temporal change in a predicted SAR value of each of the plurality of pulse sequences;
displaying a SAR graph showing the temporal change in the predicted SAR value of said each of the plurality of pulse sequences, wherein a display mode of a movable pulse sequence, for which an execution order in an execution of the plurality of pulses sequences can be changed, and a display mode of an immovable pulse sequence, for which an execution order in an execution of the plurality of pulse sequences cannot be changed, are different on the displayed SAR graph; and adjusting, in the MRI system, execution of the plurality of pulse sequences based on the displayed SAR graph, such that the predicted SAR value becomes less than an upper SAR limit.

19. The SAR adjustment method according to claim 18, further comprising:

exchanging movable pulse sequences among the plurality of pulse sequences or inserting a waiting time between some of the plurality of pulse sequences;

recalculating a temporal change in the predicted SAR value of each of the pulse sequences after the pulse sequence exchange or the waiting time insertion; and updating the SAR graph so that the pulse sequence exchange or the waiting time insertion and the recalculated predicted SAR value are displayed.

20. The SAR adjustment method according to claim 18, wherein, in displaying the SAR graph, display modes of at least two pulse sequences are made to be different on the SAR graph on the basis of the predicted SAR value of each of the at least two pulse sequences or on the basis of whether or not it is possible to exchange the at least two pulse sequences.

* * * * *